(12) United States Patent
Liu et al.

(10) Patent No.: US 9,988,364 B1
(45) Date of Patent: Jun. 5, 2018

(54) PROCESS FOR SYNTHESIS OF ELIGLUSTAT AND INTERMEDIATE COMPOUNDS THEREOF

(71) Applicant: ZHEJIANG AUSUN PHARMACEUTICAL CO., LTD., Zhejiang (CN)

(72) Inventors: Yu Liu, Zhejiang (CN); Guanneng Yu, Zhejiang (CN); Zhiguo Zheng, Zhejiang (CN)

(73) Assignee: ZHEJIANG AUSUN PHARMACEUTICAL CO., LTD., Zhejiang (CN)

( * ) Notice: Subject to any disclaimer, the term of this patent is extended or adjusted under 35 U.S.C. 154(b) by 0 days. days.

(21) Appl. No.: 15/681,716

(22) Filed: Aug. 21, 2017

Related U.S. Application Data

(63) Continuation of application No. 15/654,933, filed on Jul. 20, 2017.

(30) Foreign Application Priority Data

Mar. 21, 2017 (CN) .......................... 2017 1 0169305

(51) Int. Cl.
*C07D 319/18* (2006.01)
*C07D 405/06* (2006.01)
*A61K 31/40* (2006.01)
*A61K 31/357* (2006.01)
*C07C 231/00* (2006.01)
*C07C 209/26* (2006.01)
*C07D 207/04* (2006.01)
*A61K 31/16* (2006.01)

(52) U.S. Cl.
CPC ............ *C07D 319/18* (2013.01); *A61K 31/16* (2013.01); *A61K 31/357* (2013.01); *A61K 31/40* (2013.01); *C07C 209/26* (2013.01); *C07C 231/00* (2013.01); *C07D 207/04* (2013.01); *C07D 405/06* (2013.01); *A61K 2300/00* (2013.01)

(58) Field of Classification Search
CPC ............................. C07D 319/18; C07D 405/06
See application file for complete search history.

(56) References Cited

FOREIGN PATENT DOCUMENTS

CN 105646442 * 6/2016 ........... C07D 319/18

OTHER PUBLICATIONS

Machine Translation of CN105646442 (Jun. 2016).*

* cited by examiner

*Primary Examiner* — Robert Havlin
(74) *Attorney, Agent, or Firm* — Ladas & Parry LLP

(57) ABSTRACT

The present invention relates to a process for synthesis of Eliglustat and intermediate compounds thereof. In particular, the present invention relates to a process for synthesis of Eliglustat and pharmaceutically acceptable salts thereof, and relates to the intermediate compounds in the process and a process for preparation of the intermediate compounds.

18 Claims, No Drawings

PROCESS FOR SYNTHESIS OF ELIGLUSTAT AND INTERMEDIATE COMPOUNDS THEREOF

CROSS REFERENCE APPLICATIONS

This application is a continuation of U.S. patent application Ser. No. 15/654,933 filed Jul. 20, 2017, which claims the benefit of Chinese Application No: 201710169305.9 filed Mar. 21, 2017. This application also claims the benefit of Chinese Application No.: 201710169305.9 filed Mar. 21, 2017, the content of which is incorporated herein by reference.

TECHNICAL FIELD

The present invention relates to the field of synthesis of organic compounds. In particular, the present invention relates to a process for synthesis of Eliglustat and pharmaceutically acceptable salts thereof, and relates to the intermediate compounds in the process and a process for preparation of the intermediate compounds.

BACKGROUND ART

Gaucher disease is a disease of glucocerebroside accumulation caused by an autosomal recessive inheritance. The main reason is that deficiency of glucosylceramidase due to mutation of structural gene coding glucosylceramidase results in that glucocerebroside in macrophages cannot be further hydrolyzed and then is accumulated in the lysosome, leading to loss of the original function of the cells, thereby causing diseases in bone, bone marrow, spleen, liver and lung. Eliglustat is a glucosylceramidase inhibitor developed by Genzyme Co. as a subsidiary of Sanofi Co. The US Food and Drug Administration (FDA) approved Eliglustat as an orphan drug on Sep. 17, 2008 and formally approved it to enter the market on Aug. 19, 2014 (Trade name Cerdelga), used as a first-line oral drug for adult patients with Gaucher disease Type 1. According to an article in Journal of the American Medical Association, the oral treatment with Eliglustat resulted in significant improvements in spleen volume, hemoglobin level, liver volume and platelet count in patients with Gaucher disease Type 1.

The chemical name of Eliglustat is N-[(1R,2R)-2-(2,3-dihydro-benzo[1,4]dioxin-6-yl)-2-hydroxy-1-(pyrrolidinylmethyl)ethyl]octanamide with the structural formula below:

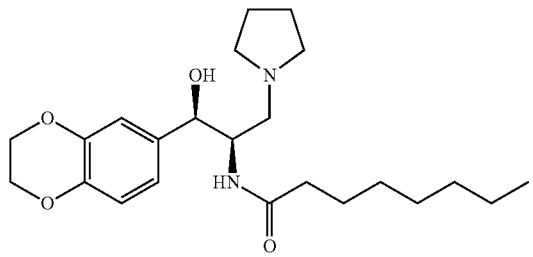 [SMILES: CCCCCCCC(=O)N[C@H](CN1CCCC1)[C@H](O)c1ccc2c(c1)OCCO2]

At present, the synthetic routes of Eliglustat mainly include:
Route I. Patent U.S. Pat. No. 7,196,205B2 reported a synthetic route as follows:
Amidation reaction of Intermediate I with Intermediate II produces the desired product.

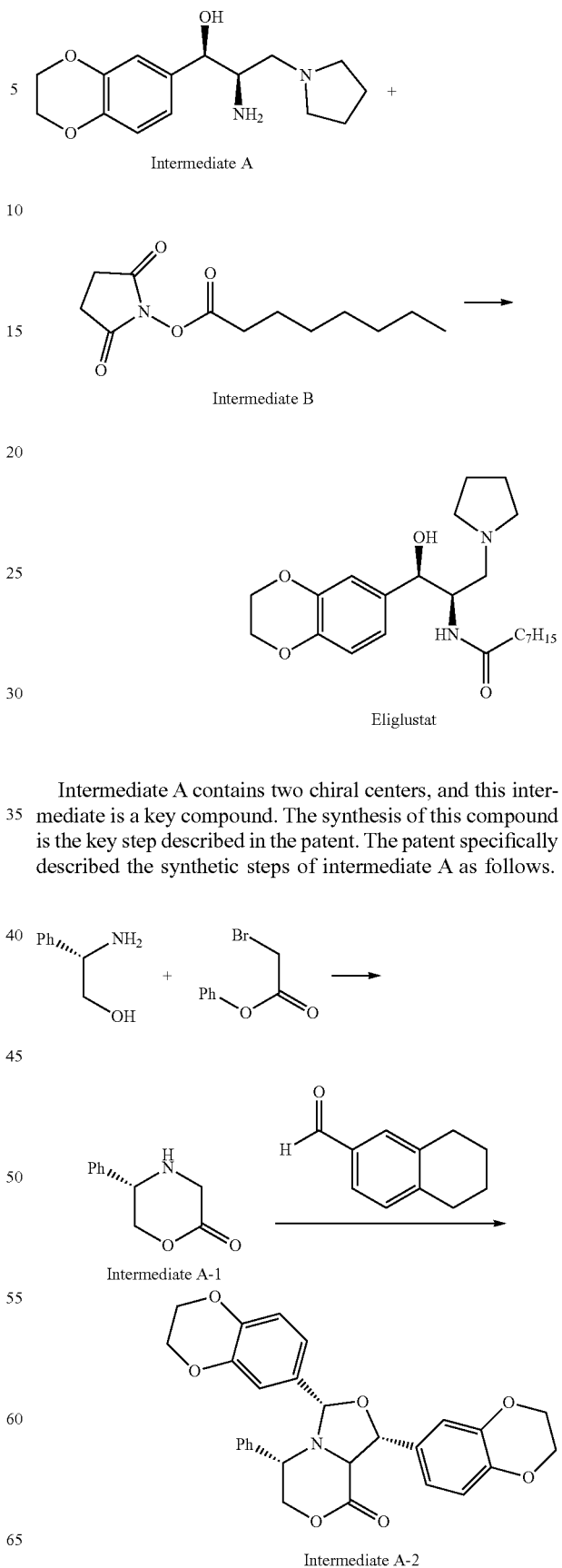

Intermediate A contains two chiral centers, and this intermediate is a key compound. The synthesis of this compound is the key step described in the patent. The patent specifically described the synthetic steps of intermediate A as follows.

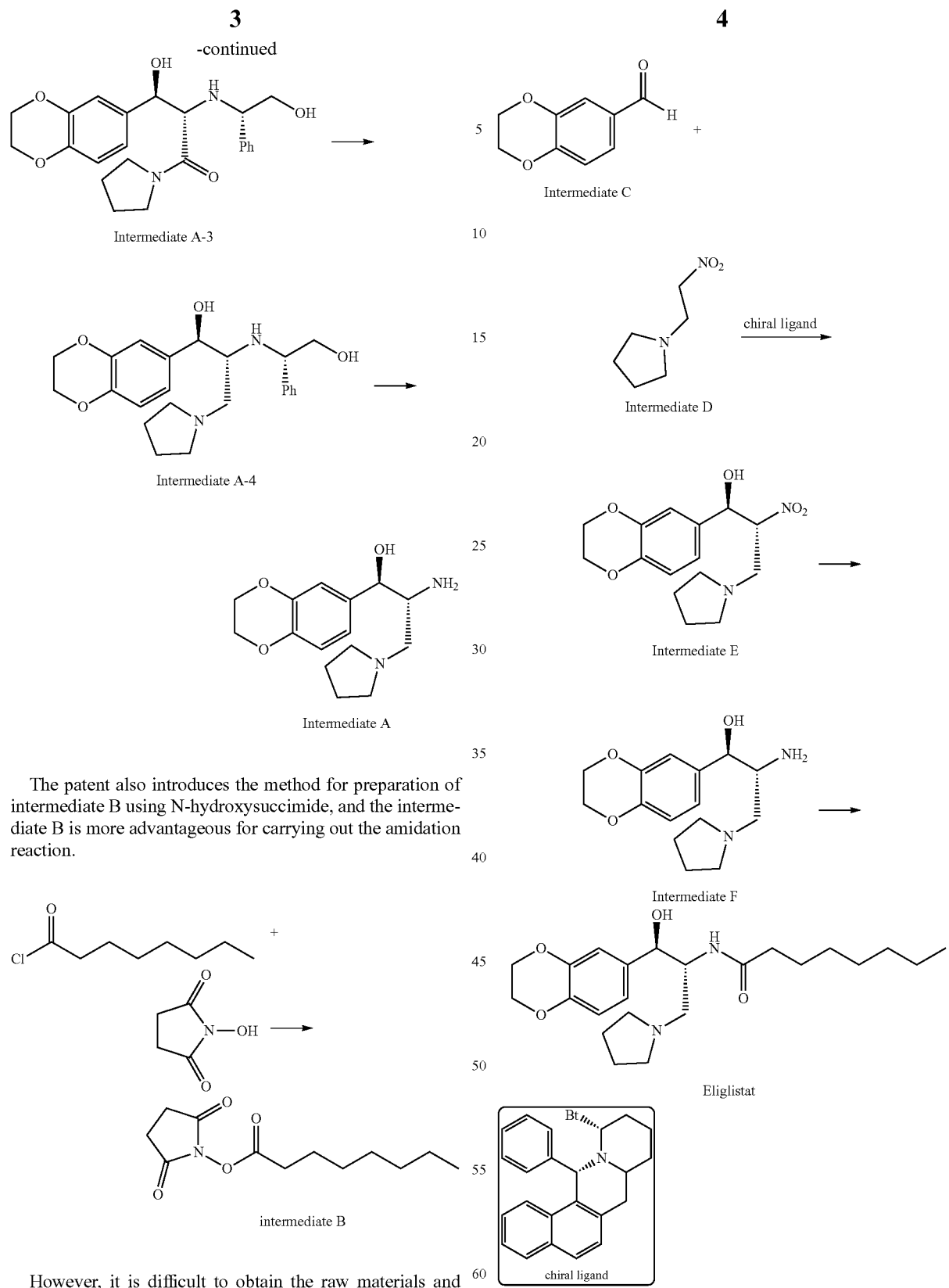

The patent also introduces the method for preparation of intermediate B using N-hydroxysuccimide, and the intermediate B is more advantageous for carrying out the amidation reaction.

However, it is difficult to obtain the raw materials and adjuvants used in the route, the catalyst is expensive, the yield is low and it is difficult to apply the method to industry.

Route II. Patent CN104557851A reported a new synthetic route for synthesis of Eliglustat. The route used intermediate C and intermediate D as the key starting materials and utilized a chiral ligand to build two chiral centers.

The patent also introduces the synthetic methods of intermediate D:

Method 1:

The reaction of pyrrolidine with halo-nitroalkane is used to give intermediate D.

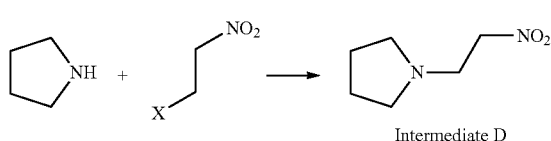

Intermediate D

Method 2:
Reduction reaction is used to give intermediate D.

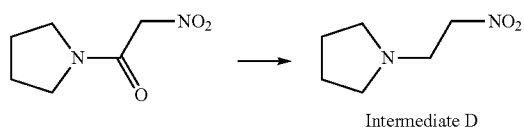 [SMILES: O=C(C[N+](=O)[O-])N1CCCC1 ; O=[N+]([O-])CCN1CCCC1]

Intermediate D

It is difficult to obtain the chiral ligand used in this route, the chiral ligand is expensive, and the key intermediate D is a nitrocompound which has risk of influencing safety in the course of its preparation and use.

Route III. Patent CN105646442A reported a method for preparation of Eliglustat. The route used intermediate G as starting material. After several reaction steps, the reaction with octanoyl chloride finally produces the desired product.

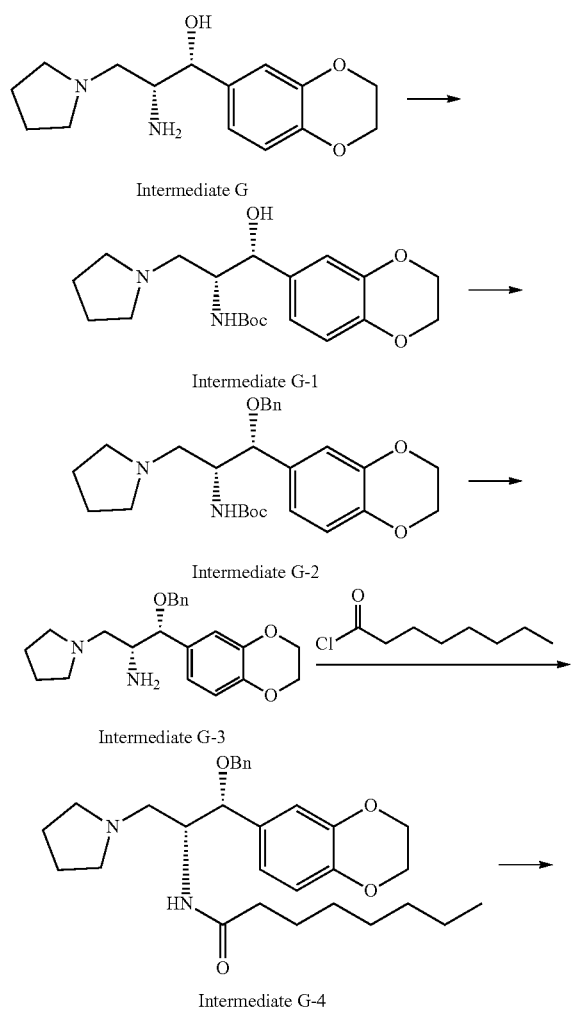

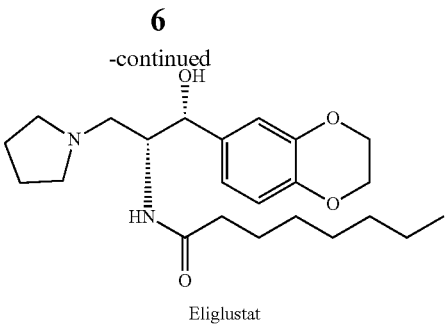

Eliglustat

This route only relates to the synthesis from intermediate G to Eliglustat, but does not teach how to synthesize intermediate G. Furthermore, multiple steps of protection and deprotection result in low yield, increased cost and more complicated operations, thus are not advantageous for industrial production.

In order to overcome the defects in the above routes, the present invention provides a new process for synthesis of Eliglustat. The process has advantages of convenient operations, high yield, good purity of intermediates and desired product, and it is easy to apply the process in the industrial production.

CONTENTS OF THE INVENTION

Throughout the description, the following terms have the meanings as indicated below.

The term "alkyl", whether it is used alone or in combination with other groups, represents a straight or branched monovalent saturated hydrocarbon group consisting of carbon atom and hydrogen atom. The term "$C_{1-6}$ alkyl" represents straight or branched alkyl having 1-6 carbon atoms, such as methyl, ethyl, n-propyl, isopropyl, n-butyl, sec-butyl, tert-butyl, and n-hexyl.

"Halo" or "Halogen" represents fluoro, chloro, bromo or iodo.

"Haloalkyl" represents alkyl as defined above which is substituted with one or more halogens, e.g., trifluoromethyl.

The term "alkoxy", whether it is used alone or in combination with other groups, represents group R'—O—, wherein R' represents alkyl as defined above. "$C_{1-6}$ alkoxy" represents group R'—O—, wherein R' represents $C_{1-6}$ alkyl as defined above.

"Haloalkoxy" represents alkoxy as defined above which is substituted with one or more halogens, e.g., trifluoromethoxy.

"Aryl" represents monocyclic or fused bicyclic aromatic ring containing carbon atoms. "$C_{5-10}$ aryl" represents aryl having 5-10 carbon atoms. For example, $C_{5-10}$ aryl may be phenyl or naphthyl.

"Aralkyl" represents alkyl as defined above which is substituted with aryl as defined above.

"Aralkoxy" represents alkoxy as defined above which is substituted with aryl as defined above.

"Acyl" represents group —CO—R, wherein R is alkyl, aryl or aralkyl as defined above.

The alkyl or aryl as mentioned above, whether it is used as itself per se or used as a part of other groups such as aralkyl and aralkoxy, may be optionally substituted with one or more substituents. In the case of "substituted alkyl", the substituents on alkyl are preferably selected from $C_{1-6}$ alkoxy, halo, aryl and nitro, more preferably selected from methoxy, ethoxy, halo, phenyl and nitro. In the case of "substituted aryl", the substituents on aryl are preferably selected from $C_{1-6}$ alkyl, $C_{1-6}$ alkoxy, halo, aryl and nitro, more preferably selected from methyl, methoxy, ethoxy, halo, phenyl and nitro.

"hydroxy-protecting reagent" refers to the reagents which can react with the compounds with hydroxyl to afford hydroxy-protecting group on the hydroxy, said hydroxy-protecting group is selected from alkyl, haloalkyl, aralkyl, alkoxyalkyl, allyl, acyl, or silyl protective group, such as t-BuMe$_2$Si, t-BuPh$_2$Si, (i-Pr)$_3$Si, Et$_3$Si, Me$_3$Si, allyl, 2-tetrahydropyranyl, methoxymethyl, formyl, acetyl, benzyl or —CH$_2$Ar, wherein Ar is unsubstituted or substituted aryl, such as p-methoxyphenyl or halogen-substituted phenyl. Those conventional hydroxy-protecting reagents which can afford hydroxy-protecting groups are well-known for a person skilled in the art, such as tert-butyldimethylsilyl chloride, trimethylsilyl chloride, benzoyl chloride, and the like.

In a first aspect, the present invention provides a process for preparation of Eliglustat and pharmaceutically acceptable salts thereof,

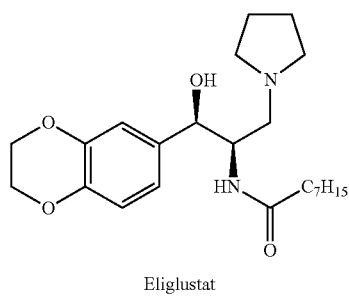

Eliglustat the process comprising the following steps:

(a-1) sulfonylation reaction of Compound V to give Compound VI,

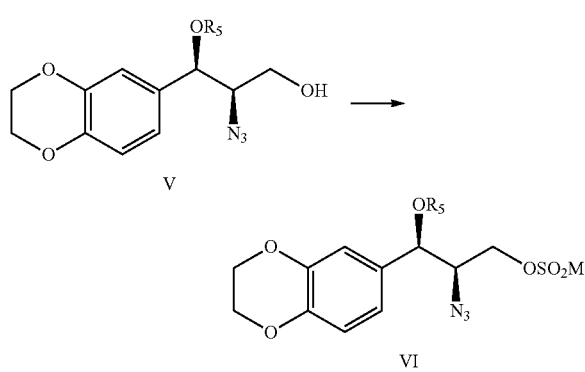

wherein R$_5$ is hydrogen or hydroxy-protecting group, said hydroxy-protecting group is selected from alkyl, haloalkyl, aralkyl, alkoxyalkyl, allyl, acyl or silyl protective group, such as t-BuMe$_2$Si, t-BuPh$_2$Si, (i-Pr)$_3$Si, Et$_3$Si, Me$_3$Si, allyl, 2-tetrahydropyranyl, methoxymethyl, formyl, acetyl, benzyl or —CH$_2$Ar, wherein Ar is unsubstituted or substituted aryl, such as p-methoxyphenyl or halogen-substituted phenyl, M is alkyl, aryl, substituted aryl or substituted alkyl, (a-2) reacting Compound VI with pyrrolidine to give Compound VII,

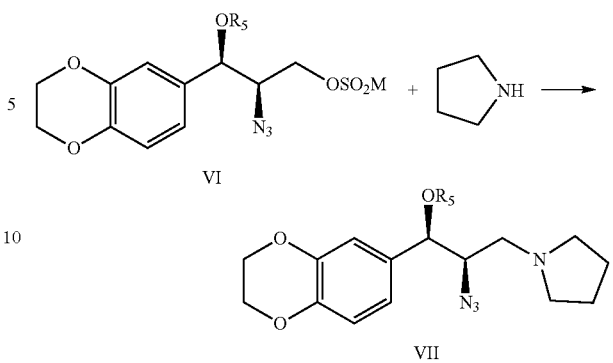

(a-3) reducing Compound VII by catalytic hydrogenation with metal catalyst or reducing Compound VII with organophosphorus reagent, to give Compound VIII,

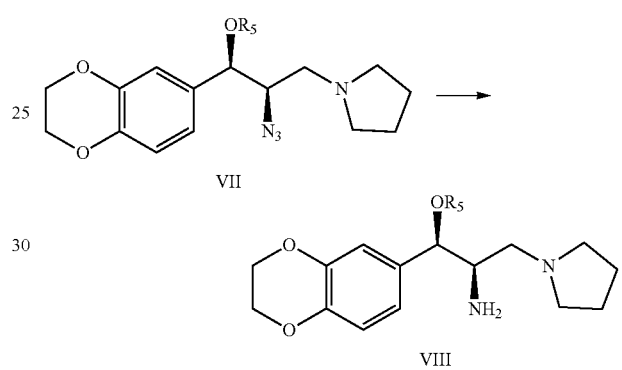

(a-4) amidation reaction of Compound VIII with Compound IX to give Compound X,

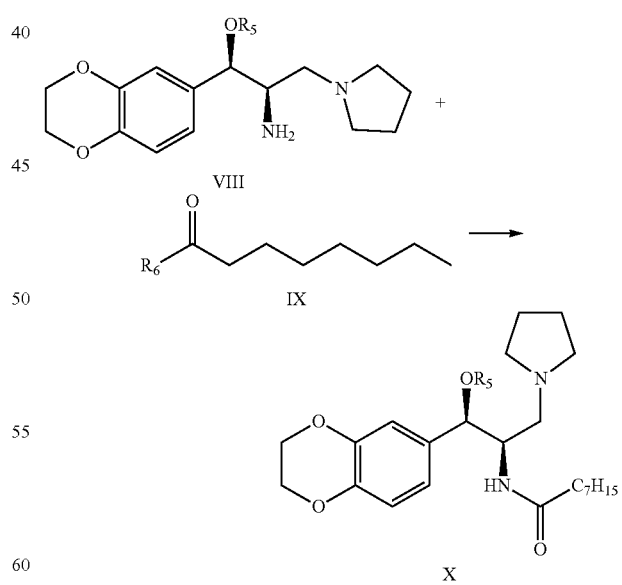

wherein R$_6$ is selected from hydroxy, halogen or succimidyloxy, when R$_5$ is hydrogen, Compound X is Eliglustat, or when R$_5$ is hydroxy-protecting group, the following step is further carried out:

(a-5) deprotecting Compound X to remove hydroxy-protecting group, to give Eliglustat

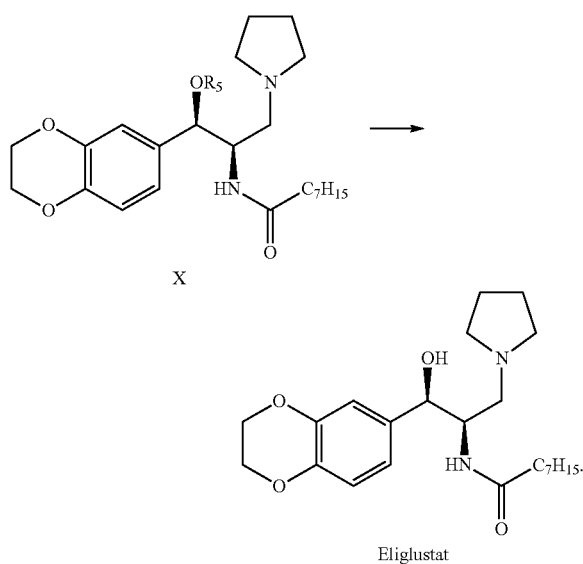

In a preferred embodiment, the $R_5$ is hydrogen or silyl protective group, such as t-BuMe$_2$Si, t-BuPh$_2$Si, (i-Pr)$_3$Si, Et$_3$Si, or Me$_3$Si.

In a preferred embodiment, the $R_6$ is chloro or succimidyloxy.

In the step (a-1), sulfonylation reaction can be carried out with sulfonyl halide, such as alkylsulfonyl chloride, arylsulfonyl chloride, substituted arylsulfonyl chloride or substituted alkylsulfonyl chloride, such as p-toluenesulfonyl chloride, phenylsulfonyl chloride, p-halophenylsulfonyl chloride, p-nitrophenyl sulfonyl chloride, o-nitrophenylsulfonyl chloride or methylsulfonyl chloride. The reaction can be carried out without catalyst or with appropriate amount of acylation catalyst, and the catalyst used may be DMAP; the base used in the reaction may be organic base which is commonly used, such as pyridine, organic tertiary amines, such as triethylamine or diisopropylethylamine. The reaction solvent is organic aprotic solvent, such as dichloromethane, chloroform, methyltetrahydrofuran, tetrahydrofuran, pyridine, toluene, ethyl acetate, acetonitrile, DMF, DMA, or a mixture of any two or more of the solvents.

In the step (a-2), pyrrolidine is reacted with the sulfonate of formula VI. The reaction solvent is organic aprotic solvent, such as dichloromethane, chloroform, methyltetrahydrofuran, tetrahydrofuran, pyridine, toluene, ethyl acetate, acetonitrile, DMF, DMA, or a mixture of any two or more of the solvents.

In the step (a-3), the metal catalyst used in the hydrogenation is Pd catalyst or Ni catalyst, such as Pd/C, Pd(OH)$_2$, Pd(OAc)$_2$, PdCl$_2$, Pd, Raney nickel, Ni; the organophosphorus reagent used is preferably triphenylphosphine. The reaction solvent is selected from alcohols, esters or ethers, or a mixture of any two or more of the solvents.

In the step (a-4):
When $R_6$ is hydroxy, the reaction of Compound VIII with Compound IX is carried out under catalysis of coupling agent to give Compound X. The reaction solvent is organic aprotic solvent, such as dichloromethane, chloroform, methyltetrahydrofuran, tetrahydrofuran, pyridine, toluene, ethyl acetate, acetonitrile, DMF, DMA, or a mixture of any two or more of the solvents. The coupling agent is the conventional coupling agent for amidation, such as EDC, DCC, HOBt, oxalyl chloride, or a mixture of any two or more thereof.

When $R_6$ is chloro or succimidyloxy, amidation reaction of Compound VIII with Compound IX yields Compound X; the reaction may be carried out without catalyst or with appropriate amount of deacid reagent, and the deacid reagent used in the reaction can be conventional organic base, such as pyridine, organic tertiary amines, such as triethylamine or diisopropylethylamine. The reaction solvent is organic aprotic solvent, such as dichloromethane, chloroform, methyltetrahydrofuran, tetrahydrofuran, pyridine, toluene, ethyl acetate, acetonitrile, DMF, DMA, or a mixture of any two or more of the solvents.

In the step (a-5):
When $R_5$ is silyl protective group, the reaction of step a-5 is carried out in the presence of base, acid or a fluorine-containing salt, the base is selected from alkali metal or alkaline earth metal hydroxide or carbonate, such as NaOH, KOH, Na$_2$CO$_3$, or K$_2$CO$_3$, and the fluorine-containing salt is preferably tetrabutylammonium fluoride (TBAF). The solvent used in the reaction is protonic solvent, such as water, methanol, ethanol, isopropanol, or a mixture of any two or more thereof.

When $R_5$ is alkyl, haloalkyl, alkoxyalkyl or allyl protective group, the reaction of step a-5 is carried out in the presence of acid. The reaction is preferably carried out in the presence of strong acid, such as trifluoroacetic acid or hydrochloric acid.

When $R_5$ is aralkyl protective group, the reaction of step a-5 is carried out under catalytic hydrogenation with metal catalyst, and the metal catalyst used in the hydrogenation is Pd catalyst or Ni catalyst, such as Pd/C, Pd(OH)$_2$, Pd(OAc)$_2$, PdCl$_2$, Pd, Raney nickel, Ni, the organophosphorus reagent used is preferably triphenylphosphine. The reaction solvent is selected from alcohols, esters or ethers, or a mixture of any two or more of the solvents.

When $R_5$ is p-methoxybenzyl, the reaction of step a-5 may be carried out in the presence of oxidizing agent. The oxidizing agent is preferably DDQ or ammonium ceric nitrate.

When $R_5$ is acyl protective group, the reaction of step a-5 is carried out under the condition of conventional deprotection to remove the acyl. For example, the deprotection may be carried out by hydrolysis with hydrochloric acid or sodium hydroxide, or by ester exchange with sodium methoxide/methanol.

In a particularly preferred embodiment of the above process, $R_5$ is hydrogen, and the process only includes the above reaction steps (a-1), (a-2), (a-3) and (a-4).

In a second aspect, the present invention provides compound of formula V:

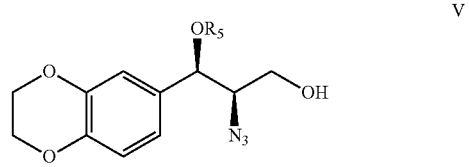

wherein $R_5$ is hydrogen or hydroxy-protecting group, said hydroxy-protecting group is selected from alkyl, haloalkyl, aralkyl, alkoxyalkyl, allyl, acyl or silyl protective group, such as t-BuMe$_2$Si, t-BuPh$_2$Si, (i-Pr)$_3$Si, Et$_3$Si, Me$_3$Si, allyl, 2-tetrahydropyranyl, methoxymethyl, formyl, acetyl, benzyl or —CH$_2$Ar, wherein Ar is unsubstituted or substituted aryl, such as p-methoxyphenyl or halogen-substituted phenyl.

In a preferred embodiment, the compound of formula V has the structure of formula XI:

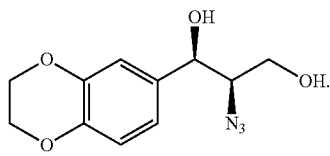

XI

In a third aspect, the present invention provides a process for preparation of the compound of formula V,

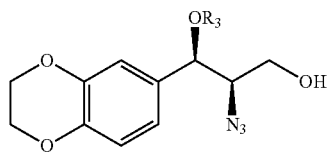

V wherein R$_5$ is hydrogen or hydroxy-protecting group, said hydroxy-protecting group is selected from alkyl, haloalkyl, aralkyl, alkoxyalkyl, allyl, acyl or silyl protective group, such as t-BuMe$_2$Si, t-BuPh$_2$Si, (i-Pr)$_3$Si, Et$_3$Si, Me$_3$Si, allyl, 2-tetrahydropyranyl, methoxymethyl, formyl, acetyl, benzyl or —CH$_2$Ar, wherein Ar is unsubstituted or substituted aryl, such as p-methoxyphenyl or halogen-substituted phenyl, the process comprising step (c-1) and step (c-3) and optional step (c-2):

(c-1) coupling reaction of Compound I with Compound II in the presence of Lewis acid, deacid reagent and coordination agent, to give Compound III.

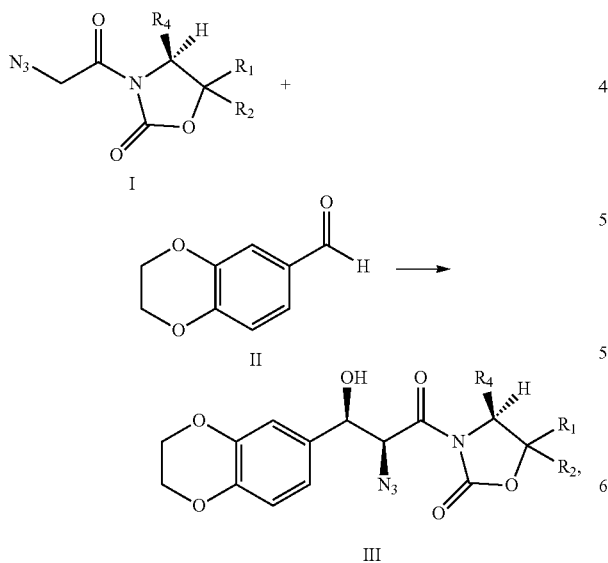

wherein each of R$_1$, R$_2$ and R$_4$, independent of each other, is selected from hydrogen, alkyl, aryl or aralkyl, such as phenyl, isopropyl or benzyl, (c-2) optionally, reacting Compound III with hydroxy-protecting reagent in the presence of base to give Compound IV, wherein R$_5$ is hydroxy-protecting group as defined above

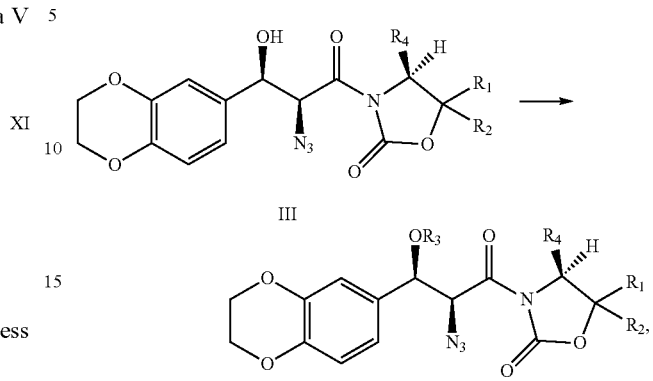

and (c-3) preparing the compound of formula V by the following steps:

(c-3.1) reducing Compound III to obtain the Compound V wherein R$_5$ is hydrogen

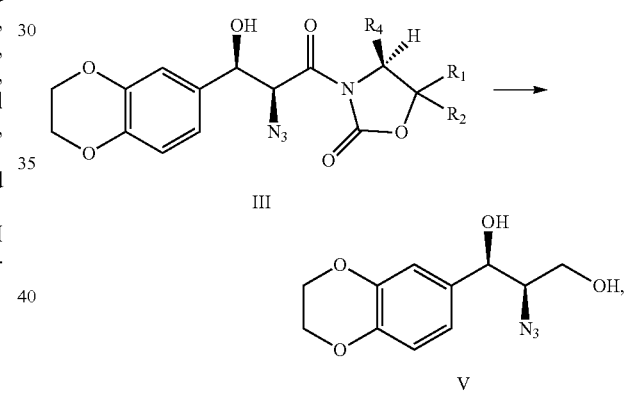

or reducing Compound IV to obtain the Compound V wherein R$_5$ is hydroxy-protecting group as defined above

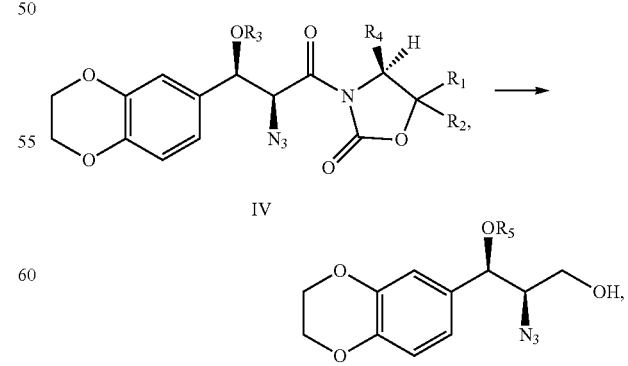

or (c-3.2) oxidizing Compound III to give Compound XI-1, and reducing Compound XI-1 to obtain the Compound V wherein $R_5$ is hydrogen (i.e, Compound XI)

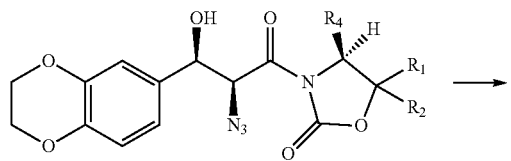

III

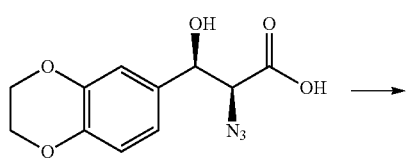

XI-1

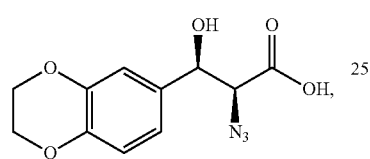

XI or oxidizing Compound IV to give Compound V-1, and reducing Compound V-1 to obtain the Compound V wherein $R_5$ is hydroxy-protecting group as defined above

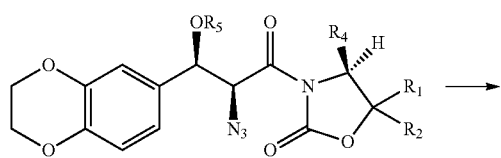

IV

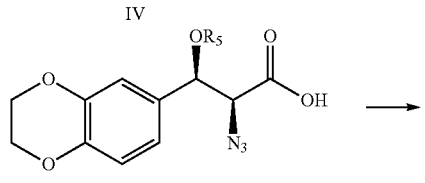

V-1

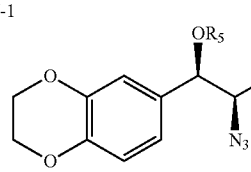

V

In a preferred embodiment, $R_1$ and $R_2$ are hydrogen and $R_4$ is phenyl or benzyl.

In another preferred embodiment, $R_4$ is isopropyl and $R_1$ and $R_2$ are phenyl.

When $R_1$ and $R_2$ are hydrogen and $R_4$ is phenyl, Compound I has the following structure (formula I-1):

I-1

Compound III has the following structure (formula III-1):

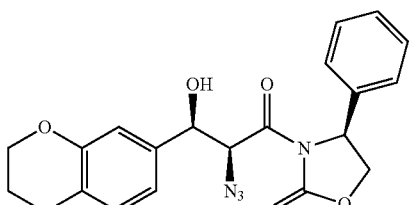

III-1

Compound IV has the following structure (formula IV-1):

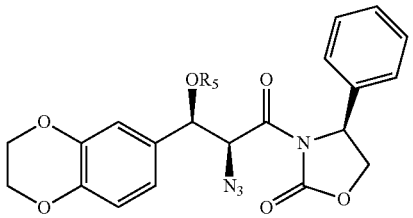

IV-1

When $R_1$ and $R_2$ are hydrogen and $R_4$ is benzyl, Compound I has the following structure (formula I-2):

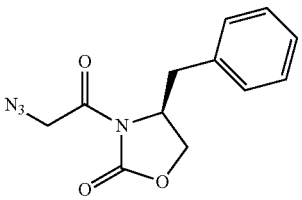

I-2

Compound III has the following structure (formula III-2):

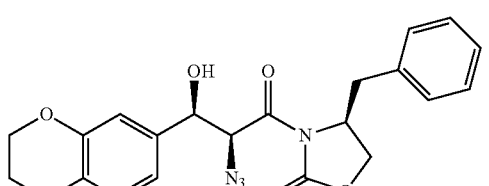

III-2

Compound IV has the following structure (formula IV-2):

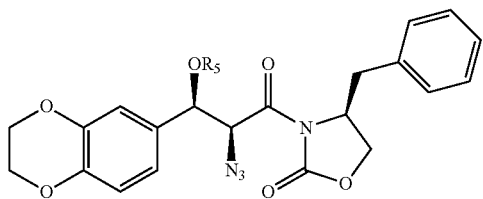

IV-2

When R₄ is isopropyl and R₁ and R₂ are phenyl, Compound I has the following structure (formula I-3):

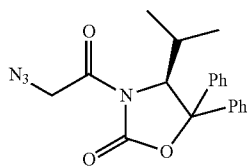

I-3

Compound III has the following structure (formula III-3):

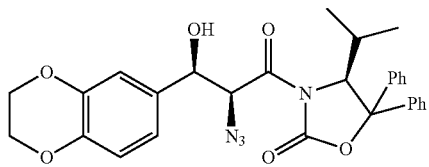

III-3

Compound IV has the following structure (formula IV-3):

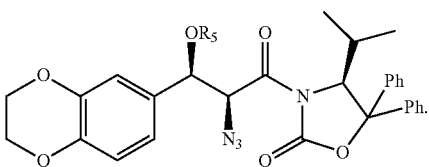

IV-3

In step c-1, the Lewis acid is preferably titanium tetrachloride or tin dichloride, the deacid reagent is organic base, such as triethylamine, pyridine, N,N-diisopropylethylamine, and the like, and the coordination agent is N-methyl pyrrolidone. The reaction temperature is −100° C. to 50° C. The reaction solvent is organic aprotic solvent, such as dichloromethane, chloroform, methyltetrahydrofuran, tetrahydrofuran, pyridine, toluene, ethyl acetate, acetonitrile. DMF, DMA, or a mixture of any two or more of the solvents.

In the optional step c-2, the reaction solvent is organic aprotic solvent, such as dichloromethane, chloroform, methyltetrahydrofuran, tetrahydrofuran, pyridine, toluene, ethyl acetate, acetonitrile, DMF, DMA, or a mixture of any two or more of the solvents. The reaction temperature is −50° C. to 100° C.

In step c-3.1, the reducing agent is selected from sodium borohydride, potassium borohydride, boron trifluoride etherate, boranes, or a mixture of any two or more thereof. The reaction solvent is selected from polar solvent, such as tetrahydrofuran, methyltetrahydrofuran, N,N-dimethyl formamide, N,N-dimethyl acetamide, water, methanol, ethanol, isopropanol, or a mixture of any two or more thereof.

In step c-3.2, the oxidizing agent is peroxide or a manganese-containing salt, such as hydrogen peroxide, tert-butyl hydroperoxide or potassium permanganate, or a mixture of any two or more thereof, the reaction can be carried out with or without catalysis of a base, and the base is selected from alkali metal or alkaline earth metal hydroxide or carbonate, such as LiOH, NaOH, KOH, Na₂CO₃, K₂CO₃. The solvent used in the oxidization reaction is protonic solvent, such as water, methanol, ethanol, isopropanol, or a mixture of any two or more thereof.

In step c-3.2, the reducing agent is selected from sodium borohydride, potassium borohydride, boron trifluoride etherate, boranes, or a mixture of any two or more thereof.

The solvent used in the reduction reaction is selected from polar solvent, such as tetrahydrofuran, methyltetrahydrofuran, N,N-dimethyl formamide, N,N-dimethyl acetamide, water, methanol, ethanol, isopropanol, or a mixture of any two or more thereof.

In a fourth aspect, the present invention provides a process for preparation of the compound of formula IV,

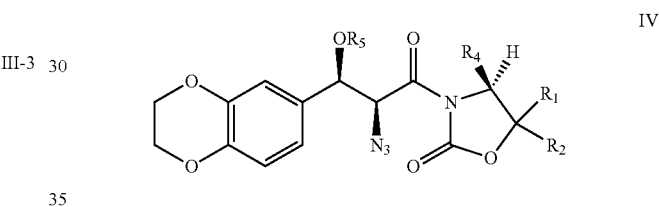

IV wherein R₅ is hydroxy-protecting group, said hydroxy-protecting group is selected from alkyl, haloalkyl, aralkyl, alkoxyalkyl, allyl, acyl or silyl protective group, such as t-BuMe₂Si, t-BuPh₂Si, (i-Pr)₃Si, Et₃Si, Me₃Si, allyl, 2-tetrahydropyranyl, methoxymethyl, formyl, acetyl, benzyl or —CH₂Ar, wherein Ar is unsubstituted or substituted aryl, such as p-methoxyphenyl or halogen-substituted phenyl, each of R₁, R₂ and R₄, independent of each other, is selected from hydrogen, alkyl, aryl or aralkyl, such as phenyl, isopropyl or benzyl, the process comprising the following steps:

(c-1) coupling reaction of Compound I with Compound II in the presence of Lewis acid, deacid reagent and coordination agent, to give Compound III,

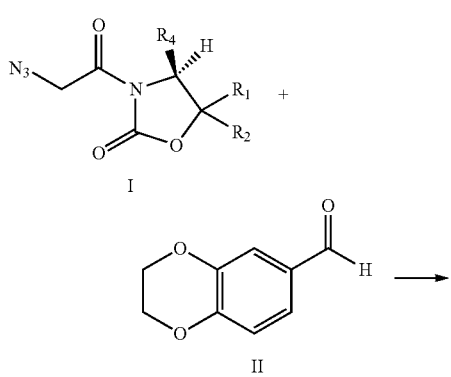

-continued

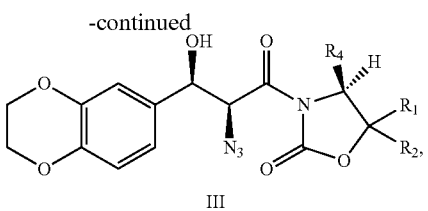

III and (c-2) reacting Compound III with hydroxy-protecting reagent in the presence of base to give Compound IV

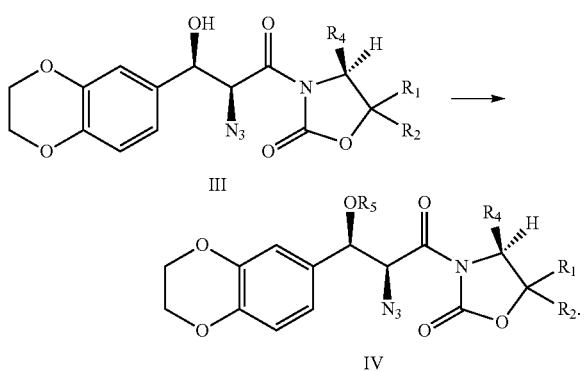

In a preferred embodiment, $R_1$ and $R_2$ are hydrogen and $R_4$ is phenyl or benzyl.

In another preferred embodiment, $R_4$ is isopropyl and $R_1$ and $R_2$ are phenyl.

The reaction conditions of step c-1 and step c-2 in the process are described as above.

In a fifth aspect, the present invention provides a process for preparation of the compound of formula III,

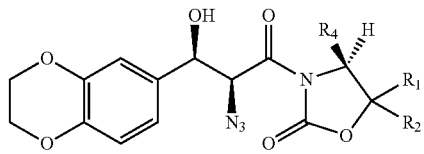

III wherein each of $R_1$, $R_2$ and $R_4$, independent of each other, is selected from hydrogen, alkyl, aryl or aralkyl, such as phenyl, isopropyl or benzyl, the process comprising the following step:

(c-1) coupling reaction of Compound I with Compound II in the presence of Lewis acid, deacid reagent and coordination agent, to give Compound III,

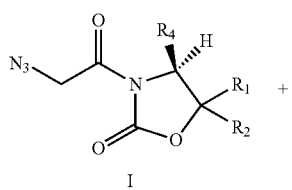

I

-continued

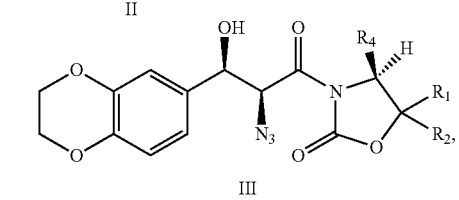

In a preferred embodiment, $R_1$ and $R_2$ are hydrogen and $R_4$ is phenyl or benzyl.

In another preferred embodiment, $R_4$ is isopropyl and $R_1$ and $R_2$ are phenyl.

The reaction condition of step c-1 in the process is described as above.

In a sixth aspect, the present invention provides a process for preparation of Eliglustat and pharmaceutically acceptable salts thereof,

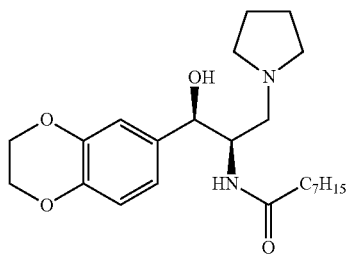

Eliglustat the process comprising the following steps:

(c-1) coupling reaction of Compound I with Compound II in the presence of Lewis acid, deacid reagent and coordination agent, to give Compound III, wherein each of $R_1$, $R_2$ and $R_4$, independent of each other, is selected from hydrogen, alkyl, aryl or aralkyl, such as phenyl, isopropyl or benzyl, (c-2) optionally, reacting Compound III with hydroxy-protecting reagent in the presence of base to give Compound IV,

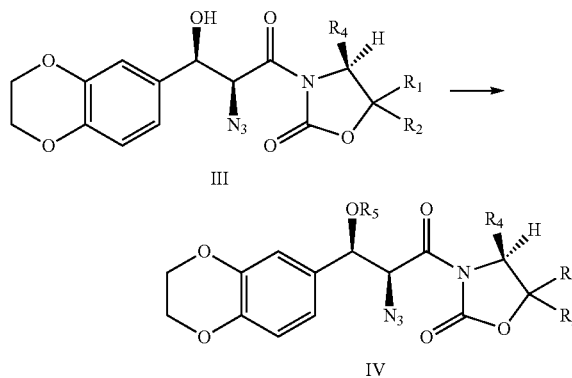

wherein $R_5$ is hydroxy-protecting group, said hydroxy-protecting group is selected from alkyl, haloalkyl, aralkyl, alkoxyalkyl, allyl, acyl or silyl protective group, such as t-BuMe$_2$Si, t-BuPh$_2$Si, (i-Pr)$_3$Si, Et$_3$Si, Me$_3$Si, allyl, 2-tetrahydropyranyl, methoxymethyl, formyl, acetyl, benzyl or —CH$_2$Ar, wherein Ar is unsubstituted or substituted aryl, such as p-methoxyphenyl or halogen-substituted phenyl; and (c-3) preparing the compound of formula V by the following steps:

(c-3.1) reducing Compound III to obtain the Compound V wherein $R_5$ is hydrogen

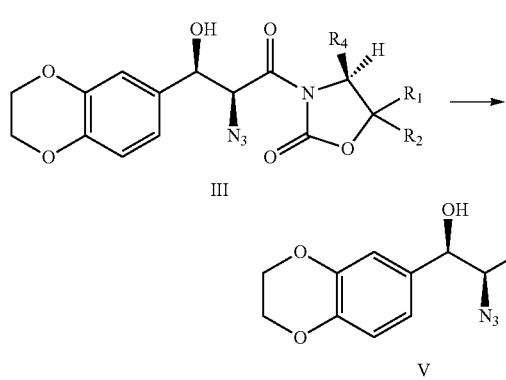

reducing Compound IV to obtain the Compound V wherein $R_5$ is hydroxy-protecting group as defined above

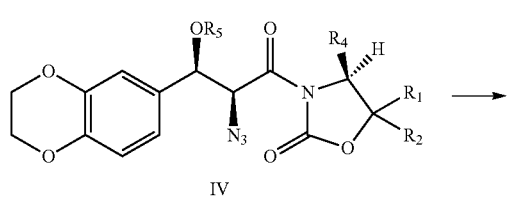

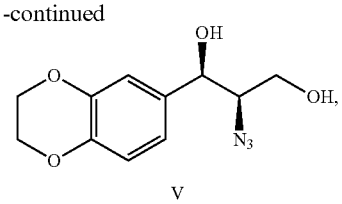

or (c-3.2) oxidizing Compound III to give Compound XI-1, and reducing Compound XI-1 to obtain the Compound V wherein $R_5$ is hydrogen (i.e, Compound XI)

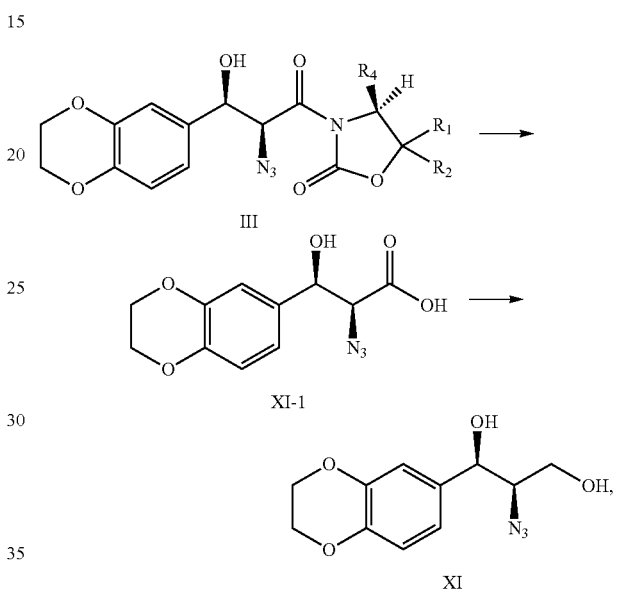

or oxidizing Compound IV to give Compound V-1, and reducing Compound V-1 to obtain the Compound V wherein $R_5$ is hydroxy-protecting group as defined above

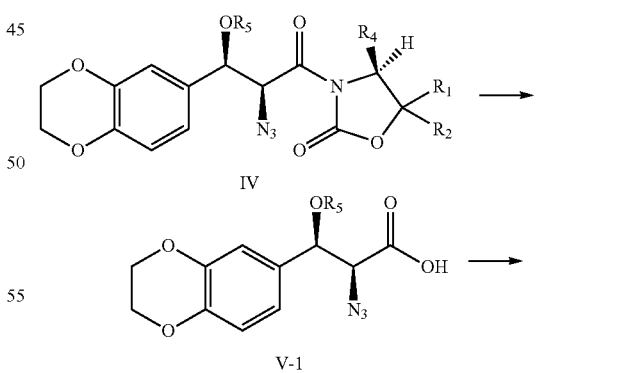

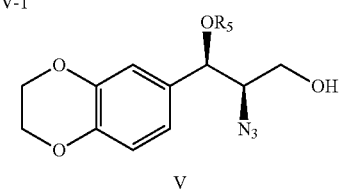

and (a-1) sulfonylation reaction of Compound V to give Compound VI,

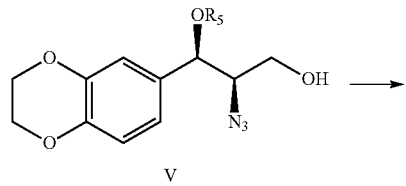

V

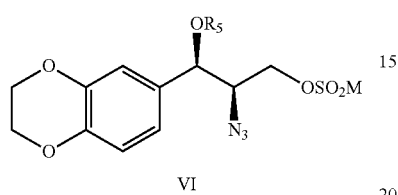

VI (a-2) reacting Compound VI with pyrrolidine to give Compound VII,

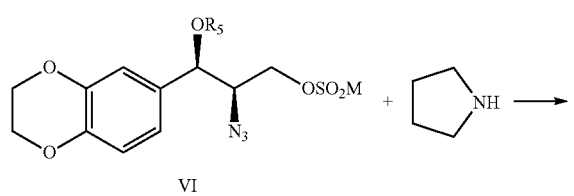

VI

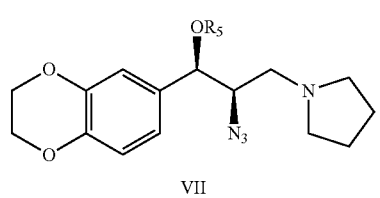

VII (a-3) reducing Compound VII by catalytic hydrogenation with metal catalyst or reducing Compound VII with organophosphorus reagent, to give Compound VIII,

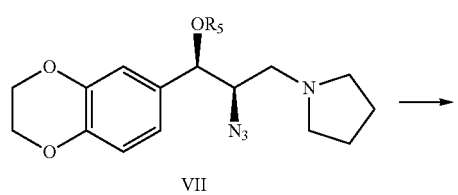

VII

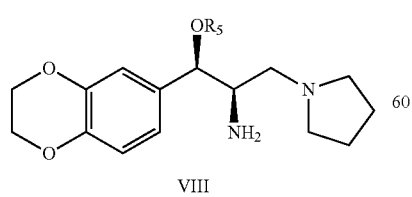

VIII (a-4) amidation reaction of Compound VIII with Compound IX to give Compound X,

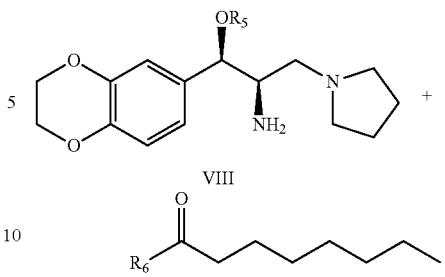

VIII

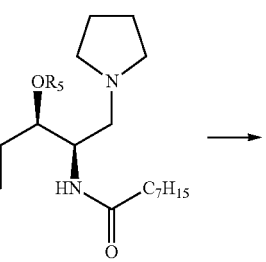

IX

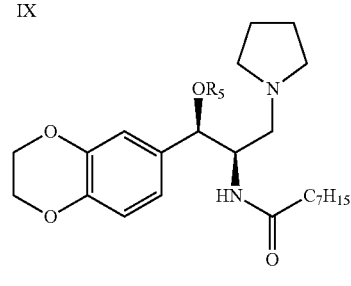

X when $R_5$ is hydrogen, Compound X is Eliglustat, or when $R_5$ is hydroxy-protecting group, the following step is further carried out:

(a-5) deprotecting Compound X to remove hydroxy-protecting group, to give Eliglustat

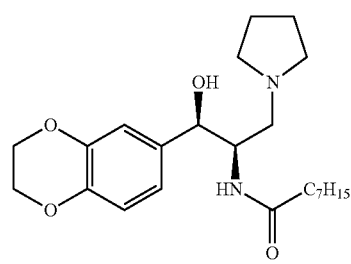

X

Eliglistat wherein:

$R_6$ is selected from hydroxy, halogen or succimidyloxy,

M is alkyl, aryl, substituted aryl or substituted alkyl.

In a preferred embodiment, $R_1$ and $R_2$ are hydrogen and $R_4$ is phenyl or benzyl.

In another preferred embodiment, $R_4$ is isopropyl and $R_1$ and $R_2$ are phenyl.

When $R_1$ and $R_2$ are hydrogen and $R_4$ is phenyl, Compound I has the following structure (formula I-1):

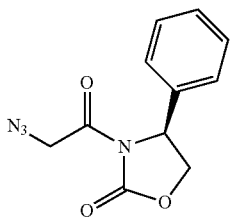

Compound III has the following structure (formula III-1):

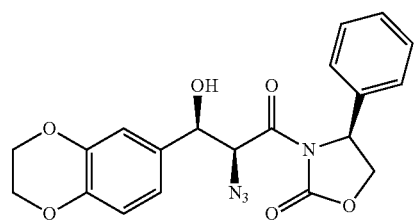

Compound IV has the following structure (formula IV-1):

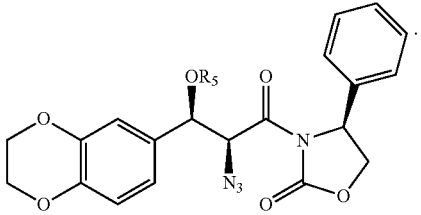

When $R_1$ and $R_2$ are hydrogen and $R_4$ is benzyl, Compound I has the following structure (formula I-2):

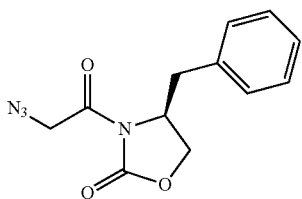

Compound III has the following structure (formula III-2):

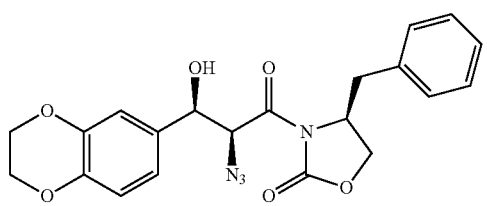

Compound IV has the following structure (formula IV-2):

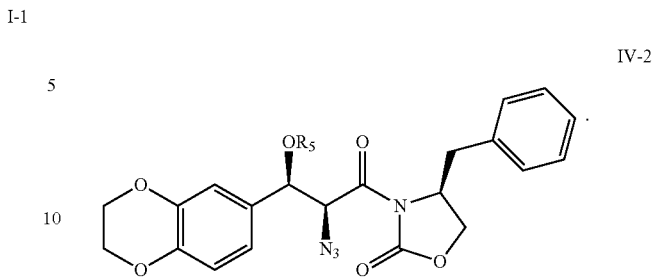

When $R_1$ and $R_2$ are phenyl and $R_4$ is isopropyl, Compound I has the following structure (formula I-3):

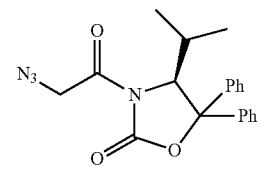

Compound III has the following structure (formula III-3):

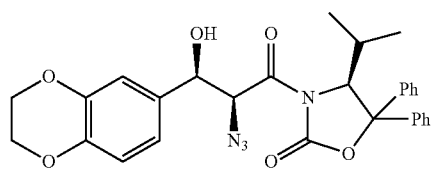

Compound IV has the following structure (formula IV-3):

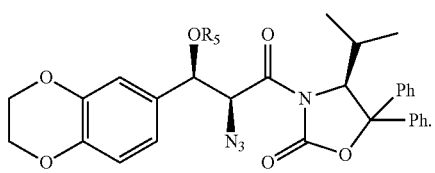

In another preferred embodiment, $R_6$ is chloro or succimidyloxy.

In another preferred embodiment, $R_5$ is hydrogen or silyl protective group.

According to a preferred embodiment of the process, in step c-1, the Lewis acid is preferably titanium tetrachloride or tin dichloride, the deacid reagent is organic base, such as triethylamine, pyridine, N,N-diisopropylethylamine, and the like, and the coordination agent is N-methyl pyrrolidone. The reaction temperature is −100° C. to 50° C. The reaction solvent is organic aprotic solvent, such as dichloromethane, chloroform, methyltetrahydrofuran, tetrahydrofuran, pyridine, toluene, ethyl acetate, acetonitrile, DMF, DMA, or a mixture of any two or more of the solvents.

In the optional step c-2, the reaction solvent is organic aprotic solvent, such as dichloromethane, chloroform, methyltetrahydrofuran, tetrahydrofuran, pyridine, toluene, ethyl acetate, acetonitrile, DMF, DMA, or a mixture of any two or more of the solvents, The reaction temperature is −50° C. to 100° C.

In step c-3.1, the reducing agent is selected from sodium borohydride, potassium borohydride, boron trifluoride etherate, boranes, or a mixture of any two or more thereof. The solvent in the reduction reaction is selected from polar solvent, such as tetrahydrofuran, methyltetrahydrofuran, N,N-dimethyl formamide, N,N-dimethyl acetamide, water, methanol, ethanol, isopropanol, or a mixture of any two or more thereof.

In step c-3.2, the oxidizing agent is peroxide or a manganese-containing salt, such as hydrogen peroxide, tert-butyl hydroperoxide or potassium permanganate, or a mixture of any two or more thereof, the reaction can be carried out with or without catalysis of a base, and the base is selected from alkali metal or alkaline earth metal hydroxide or carbonate, such as LiOH, NaOH, KOH, $Na_2CO_3$, $K_2CO_3$. The solvent used in the oxidization reaction is protonic solvent, such as water, methanol, ethanol, isopropanol, or a mixture of any two or more thereof.

In step c-3.2, the reducing agent is selected from sodium borohydride, potassium borohydride, boron trifluoride etherate, boranes, or a mixture of any two or more thereof. The solvent used in the reduction reaction is selected from polar solvent, such as tetrahydrofuran, methyltetrahydrofuran, N,N-dimethyl formamide, N,N-dimethyl acetamide, water, methanol, ethanol, isopropanol, or a mixture of any two or more thereof.

According to a further preferred embodiment of the process, in the step (a-1), sulfonylation reaction can be carried out with sulfonyl halide, such as alkylsulfonyl chloride, arylsulfonyl chloride, substituted arylsulfonyl chloride or substituted alkylsulfonyl chloride, such as p-toluenesulfonyl chloride, phenylsulfonyl chloride, p-halophenylsulfonyl chloride, p-nitrophenylsulfonyl chloride, o-nitrophenylsulfonyl chloride or methylsulfonyl chloride. The reaction can be carried out without catalyst or with appropriate amount of acylation catalyst, and the catalyst used may be DMAP; the base used in the reaction may be organic base which is commonly used, such as pyridine, organic tertiary amines, such as triethylamine or diisopropylethylamine. The reaction solvent is organic aprotic solvent, such as dichloromethane, chloroform, methyltetrahydrofuran, tetrahydrofuran, pyridine, toluene, ethyl acetate, acetonitrile, DMF, DMA, or a mixture of any two or more of the solvents.

In the step (a-2), pyrrolidine is reacted with the sulfonate of formula VI. The reaction solvent is organic aprotic solvent, such as dichloromethane, chloroform, methyltetrahydrofuran, tetrahydrofuran, pyridine, toluene, ethyl acetate, acetonitrile, DMF, DMA, or a mixture of any two or more of the solvents; In the step (a-3), the metal catalyst used in the hydrogenation is Pd catalyst or Ni catalyst, such as Pd/C, $Pd(OH)_2$, $Pd(OAc)_2$, $PdCl_2$, Pd, Raney nickel, Ni; the organophosphorus reagent used is preferably triphenylphosphine. The reaction solvent is selected from alcohols, esters or ethers, or a mixture of any two or more of the solvents.

In the step (a-4):

When $R_6$ is hydroxy, the reaction of Compound VIII with Compound IX is carried out under catalysis of coupling agent to give Compound X. The reaction solvent is organic aprotic solvent, such as dichloromethane, chloroform, methyltetrahydrofuran, tetrahydrofuran, pyridine, toluene, ethyl acetate, acetonitrile, DMF, DMA, or a mixture of any two or more of the solvents. The coupling agent is the conventional coupling agent for amidation, such as EDC, DCC, HOBt, oxalyl chloride, or a mixture of any two or more thereof.

When $R_6$ is chloro or succimidyloxy, amidation reaction of Compound VIII with Compound IX yields Compound X; the reaction may be carried out without catalyst or with appropriate amount of deacid reagent, and the deacid reagent used in the reaction can be conventional organic base, such as pyridine, organic tertiary amines, such as triethylamine or diisopropylethylamine. The reaction solvent is organic aprotic solvent, such as dichloromethane, chloroform, methyltetrahydrofuran, tetrahydrofuran, pyridine, toluene, ethyl acetate, acetonitrile, DMF, DMA, or a mixture of any two or more of the solvents.

According to another preferred embodiment of the process, the reaction condition of step (a-5) is as follows:

When $R_5$ is silyl protective group, the reaction of step a-5 is carried out in the presence of base, acid or a fluorine-containing salt, preferably in the presence of a base or a fluorine-containing salt, the base is selected from alkali metal or alkaline earth metal hydroxide or carbonate, such as NaOH, KOH, $Na_2CO_3$, $K_2CO_3$, and the fluorine-containing salt is preferably tetrabutylammonium fluoride (TBAF). The solvent used in the reaction is protonic solvent, such as water, methanol, ethanol, isopropanol, or a mixture of any two or more thereof.

When $R_5$ is alkyl, haloalkyl, alkoxyalkyl or allyl protective group, the reaction of step a-5 is carried out in the presence of acid. The reaction is preferably carried out in the presence of strong acid, such as trifluoroacetic acid or hydrochloric acid.

When $R_5$ is aralkyl protective group, the reaction of step a-5 is carried out under catalytic hydrogenation with metal catalyst, and the metal catalyst used in the hydrogenation is Pd catalyst or Ni catalyst, such as Pd/C, $Pd(OH)_2$, $Pd(OAc)_2$, $PdCl_2$, Pd, Raney nickel, Ni. The organophosphorus reagent used is preferably triphenylphosphine. The reaction solvent is selected from alcohols, esters or ethers, or a mixture of any two or more of the solvents.

When $R_5$ is p-methoxybenzyl, the reaction of step a-5 may be carried out in the presence of oxidizing agent. The oxidizing agent is preferably DDQ or ammonium ceric nitrate.

When $R_5$ is acyl protective group, the reaction of step a-5 is carried out under the condition of conventional deprotection to remove the acyl. For example, the deprotection may be carried out by hydrolysis with hydrochloric acid or sodium hydroxide, or by ester exchange with sodium methoxide/methanol.

In a particularly preferred embodiment of the process, $R_5$ is hydrogen, and the process only includes the reaction steps c-1, c-3, a-1, a-2, a-3 and a-4.

In a seventh aspect, the present invention provides a process for preparation of Eliglustat and pharmaceutically acceptable salts thereof,

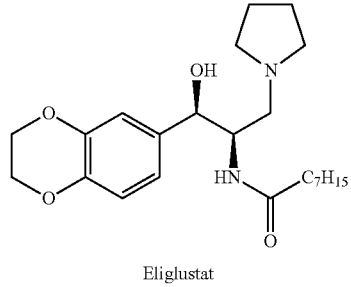

Eliglustat the process comprising the following steps:

(a-3) reducing Compound VII by catalytic hydrogenation with metal catalyst or reducing Compound VII with organophosphorus reagent, to give Compound VIII,

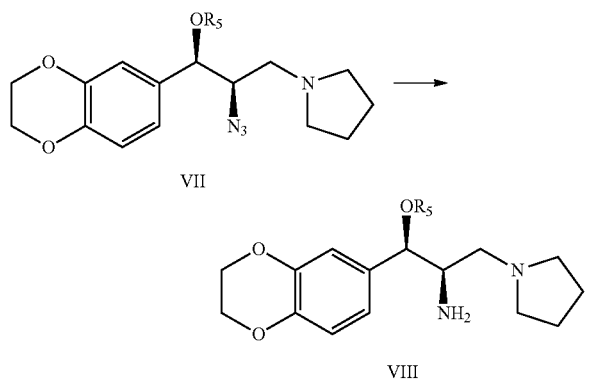

VII

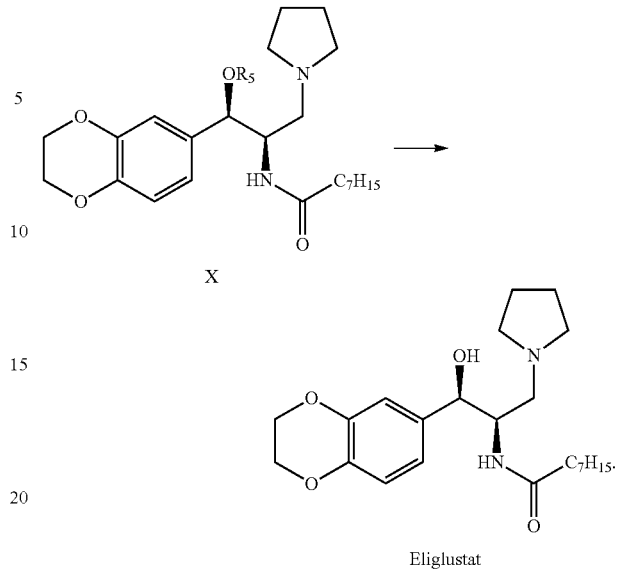

X

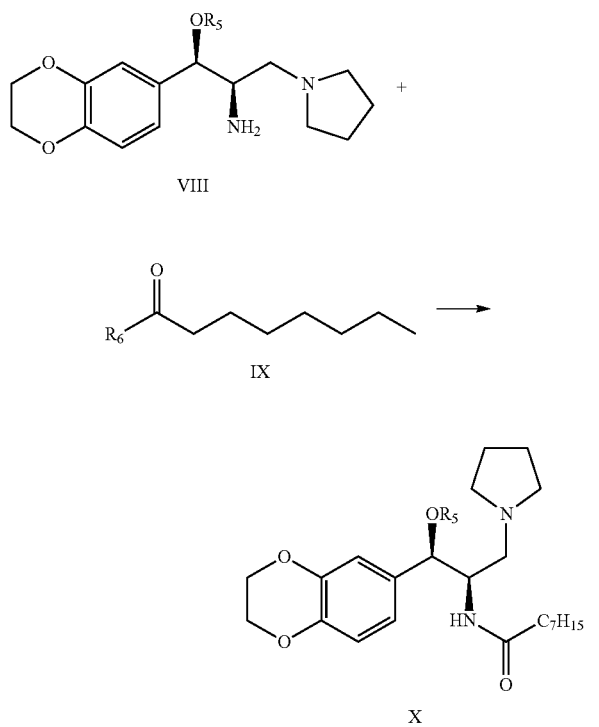

Eliglustat wherein R$_5$ is hydrogen or hydroxy-protecting group, said hydroxy-protecting group is selected from alkyl, haloalkyl, aralkyl, alkoxyalkyl, allyl, acyl or silyl protective group, such as t-BuMe$_2$Si, t-BuPh$_2$Si, (i-Pr)$_3$Si, Et$_3$Si, Me$_3$Si, allyl, 2-tetrahydropyranyl, methoxymethyl, formyl, acetyl, benzyl or —CH$_2$Ar, wherein Ar is unsubstituted or substituted aryl, such as p-methoxyphenyl or halogen-substituted phenyl, (a-4) amidation reaction of Compound VIII with Compound IX to give Compound X, wherein R$_6$ is selected from hydroxy, halogen or succimidyloxy, when R$_5$ is hydrogen, Compound X is Eliglustat, or when R$_5$ is hydroxy-protecting group, the following step is further carried out:

(a-5) deprotecting Compound X to remove hydroxy-protecting group, to give Eliglustat In a preferred embodiment, the R$_5$ is hydrogen or silyl protective group, such as t-BuMe$_2$Si, t-BuPh$_2$Si, (i-Pr)$_3$Si, or Et$_3$Si.

In another preferred embodiment, the R$_6$ is chloro or succimidyloxy.

In a further preferred embodiment, in the step (a-3), the metal catalyst used in the hydrogenation is Pd catalyst or Ni catalyst, such as Pd/C, Pd(OH)$_2$, Pd(OAc)$_2$, PdCl$_2$, Pd, Raney nickel, Ni; the organophosphorus reagent used is preferably triphenylphosphine. The reaction solvent is selected from alcohols, esters or ethers, or a mixture of any two or more of the solvents.

In the step (a-4):

When R$_6$ is hydroxy, the reaction of Compound VIII with Compound IX is carried out under catalysis of coupling agent to give Compound X. The reaction solvent is organic aprotic solvent, such as dichloromethane, chloroform, methyltetrahydrofuran, tetrahydrofuran, pyridine, toluene, ethyl acetate, acetonitrile, DMF, DMA, or a mixture of any two or more of the solvents. The coupling agent is the conventional coupling agent for amidation, such as EDC, DCC, HOBt, oxalyl chloride, or a mixture of any two or more thereof.

When R$_6$ is chloro or succimidyloxy, amidation reaction of Compound VIII with Compound IX yields Compound X. The reaction may be carried out without catalyst or with appropriate amount of deacid reagent, and the deacid reagent used in the reaction can be conventional organic base, such as pyridine, organic tertiary amines, such as triethylamine or diisopropylethylamine. The reaction solvent is organic aprotic solvent, such as dichloromethane, chloroform, methyltetrahydrofuran, tetrahydrofuran, pyridine, toluene, ethyl acetate, acetonitrile, DMF, DMA, or a mixture of any two or more of the solvents.

In another preferred embodiment, the reaction condition of step (a-5) is as follows:

When R$_5$ is silyl protective group, the reaction of step a-5 is carried out in the presence of base, acid or a fluorine-containing salt, preferably in the presence of a base or a fluorine-containing salt, the base is selected from alkali metal or alkaline earth metal hydroxide or carbonate, such as NaOH, KOH, Na$_2$CO$_3$, K$_2$CO$_3$, and the fluorine-containing salt is preferably tetrabutylammonium fluoride (TBAF). The solvent used in the reaction is protonic solvent, such as water, methanol, ethanol, isopropanol, or a mixture of any two or more thereof.

When $R_5$ is alkyl, haloalkyl, alkoxyalkyl or allyl protective group, the reaction of step a-5 is carried out in the presence of acid. The reaction is preferably carried out in the presence of strong acid, such as trifluoroacetic acid or hydrochloric acid;

When $R_5$ is aralkyl protective group, the reaction of step a-5 is carried out under catalytic hydrogenation with metal catalyst, and the metal catalyst used in the hydrogenation is Pd catalyst or Ni catalyst, such as Pd/C, Pd(OH)$_2$, Pd(OAc)$_2$, PdCl$_2$, Pd, Raney nickel, Ni; the organophosphorus reagent used is preferably triphenylphosphine. The reaction solvent is selected from alcohols, esters or ethers, or a mixture of any two or more of the solvents.

When $R_5$ is p-methoxybenzyl, the reaction of step a-5 may be carried out in the presence of oxidizing agent. The oxidizing agent is preferably DDQ or ammonium ceric nitrate.

When $R_5$ is acyl protective group, the reaction of step a-5 is carried out under the condition of conventional deprotection to remove the acyl. For example, the deprotection may be carried out by hydrolysis with hydrochloric acid or sodium hydroxide, or by ester exchange with sodium methoxide/methanol.

In a particularly preferred embodiment, $R_5$ is hydrogen, and the process only includes the above reaction steps (a-3) and (a-4).

In an eighth aspect, the present invention provides the compound of formula VII:

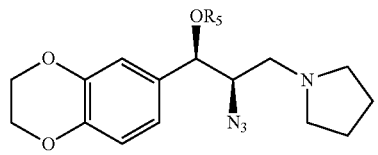

VII wherein $R_5$ is hydrogen or hydroxy-protecting group, said hydroxy-protecting group is selected from alkyl, haloalkyl, aralkyl, alkoxyalkyl, allyl, acyl or silyl protective group, such as t-BuMe$_2$Si, t-BuPh$_2$Si, (i-Pr)$_3$Si, Et$_3$Si, Me$_3$Si, allyl, 2-tetrahydropyranyl, methoxymethyl, formyl, acetyl, benzyl or —CH$_2$Ar, wherein Ar is unsubstituted or substituted aryl, such as p-methoxyphenyl or halogen-substituted phenyl.

In a preferred embodiment, the compound of formula VII has the structure of formula XII

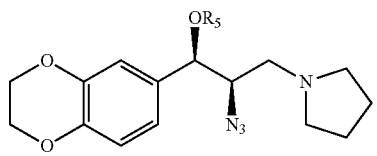

XII

In a ninth aspect, the present invention provides a process for preparation of the compound of formula VII,

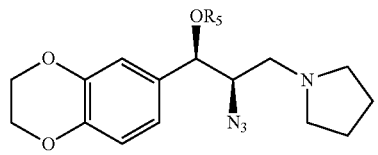

VII wherein $R_5$ is hydrogen or hydroxy-protecting group; said hydroxy-protecting group is selected from alkyl, haloalkyl, aralkyl, alkoxyalkyl, allyl, acyl or silyl protective group, such as t-BuMe$_2$Si, t-BuPh$_2$Si, (i-Pr)$_3$Si, Et$_3$Si, Me$_3$Si, allyl, 2-tetrahydropyranyl, methoxymethyl, formyl, acetyl, benzyl or —CH$_2$Ar, wherein Ar is unsubstituted or substituted aryl, such as p-methoxyphenyl or halogen-substituted phenyl.

the process comprising the following steps:

(a-1) sulfonylation reaction of Compound V to give Compound VI,

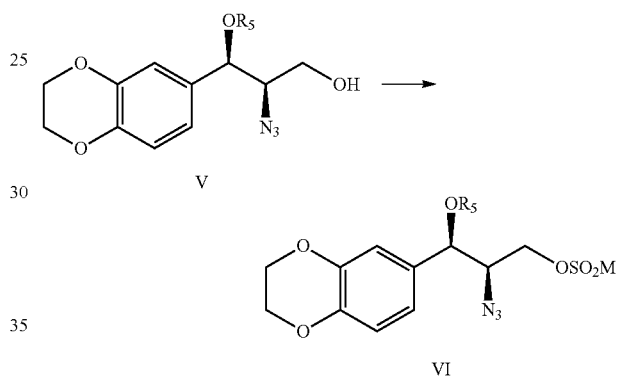

wherein M is alkyl, aryl, substituted aryl or substituted alkyl, (a-2) reacting Compound VI with pyrrolidine to give Compound VII,

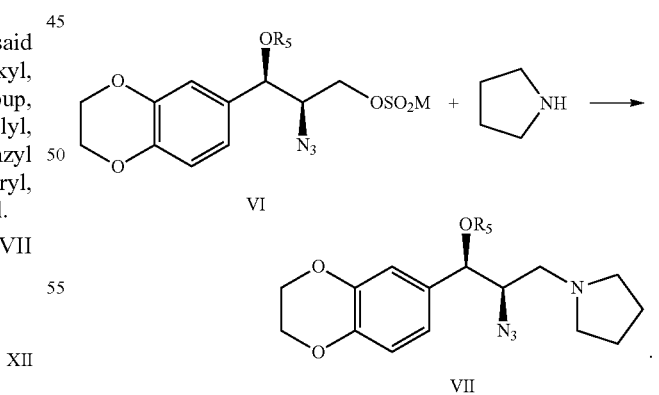

In a further preferred embodiment, the present invention provides a process for preparation of the compound of formula VII, comprising the following steps:

(c-1) coupling reaction of Compound I with Compound II in the presence of Lewis acid, deacid reagent and coordination agent, to give Compound III,

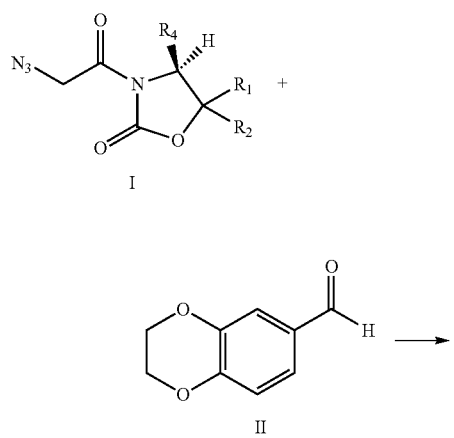

I

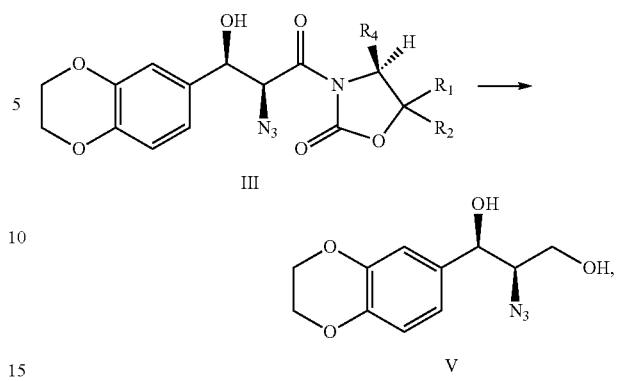

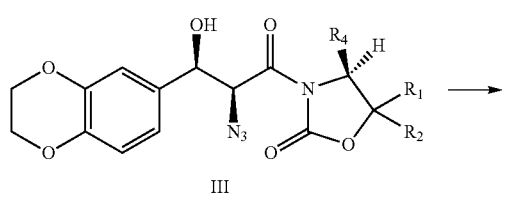

II

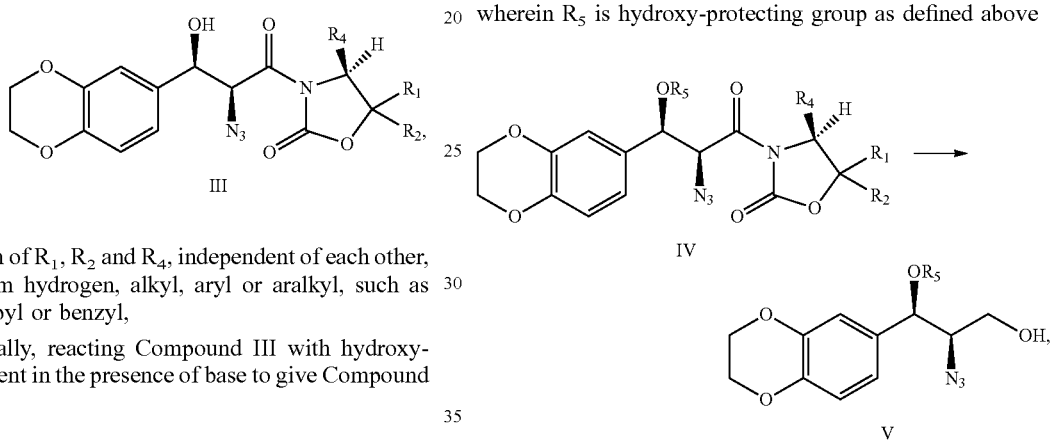

III wherein each of $R_1$, $R_2$ and $R_4$, independent of each other, is selected from hydrogen, alkyl, aryl or aralkyl, such as phenyl, isopropyl or benzyl, (c-2) optionally, reacting Compound III with hydroxy-protecting reagent in the presence of base to give Compound IV,

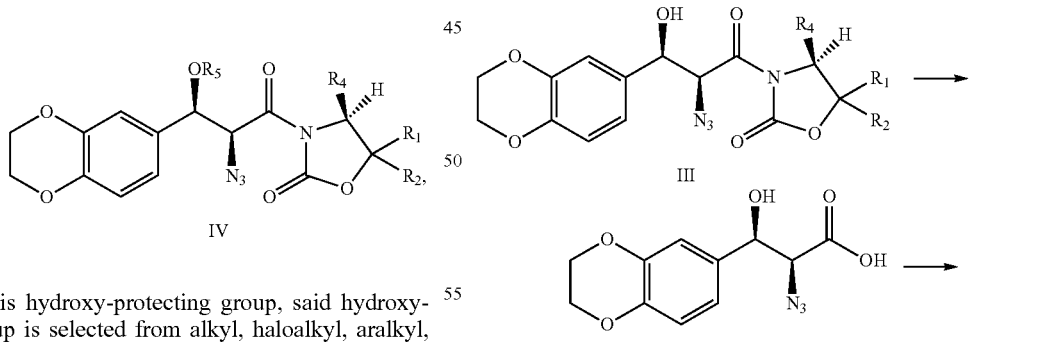

III

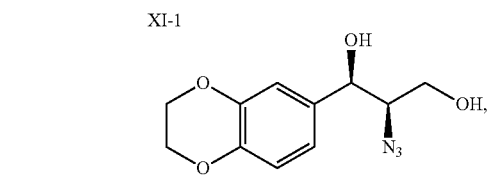

IV wherein $R_5$ is hydroxy-protecting group, said hydroxy-protecting group is selected from alkyl, haloalkyl, aralkyl, alkoxyalkyl, allyl, acyl or silyl protective group, such as t-BuMe$_2$Si, t-BuPh$_2$Si, (i-Pr)$_3$Si, Et$_3$Si, Me$_3$Si, allyl, 2-tetrahydropyranyl, methoxymethyl, formyl, acetyl, benzyl or —CH$_2$Ar, wherein Ar is unsubstituted or substituted aryl, such as p-methoxyphenyl or halogen-substituted phenyl; and (c-3) preparing the compound of formula V by the following steps:

(c-3.1) reducing Compound III to obtain the Compound V wherein $R_5$ is hydrogen or reducing Compound IV to obtain the Compound V wherein $R_5$ is hydroxy-protecting group as defined above or (c-3.2) oxidizing Compound III to give Compound XI-1, and reducing Compound XI-1 to obtain the Compound V wherein $R_5$ is hydrogen (i.e, Compound XI)

or oxidizing Compound IV to give Compound V-1, and reducing Compound V-1 to obtain the Compound V wherein R$_5$ is hydroxy-protecting group as defined above

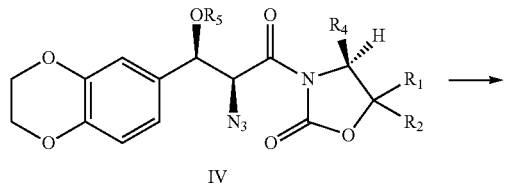

IV

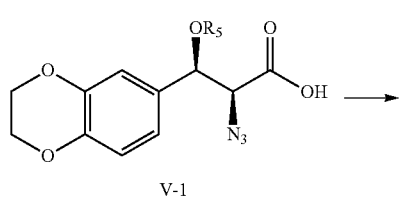

V-1

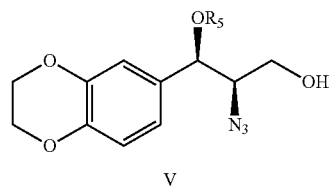

V and (a-1) sulfonylation reaction of Compound V to give Compound VI,

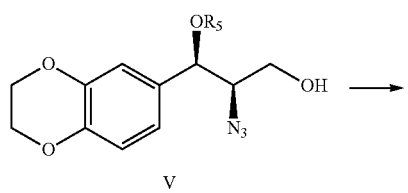

V

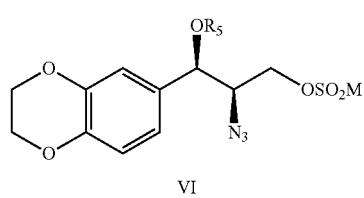

VI wherein M is alkyl, aryl, substituted aryl or substituted alkyl, (a-2) reacting Compound VI with pyrrolidine to give Compound VII,

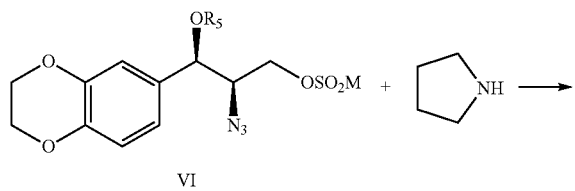

VI

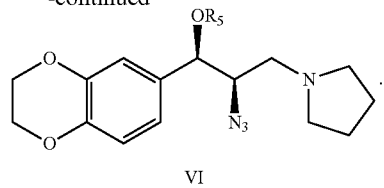

VI

In a preferred embodiment, R$_1$ and R$_2$ are hydrogen and R$_4$ is phenyl or benzyl.

In another preferred embodiment, R$_4$ is isopropyl and R$_1$ and R$_2$ are phenyl.

In another preferred embodiment, R$_5$ is silyl protective group, such as t-BuMe$_2$Si, t-BuPh$_2$Si, (i-Pr)$_3$Si, or Et$_3$Si.

In a particularly preferred embodiment, R$_5$ is hydrogen, and the process only includes the reaction steps c-1, c-3, a-1 and a-2.

In the above process, the reaction conditions of steps c-1, c-2, c-3, a-1 and a-2 are described as above.

Compared with the prior art, the process for preparation of Eliglustat and the key intermediates thereof provided by the present invention have advantages that it is easy to obtain the raw materials, the technology of the process is concise, is safe and is friendly to the environment. Moreover, the overall yield of the process is high, the product has good purity and the quality thereof is stable. Therefore, the present invention is useful for industrial production of the active pharmaceutical ingredient and for reduction of costs.

EXAMPLES

The embodiments of the present invention will be further illustrated by the following examples. It should be understood that the following examples are provided to help further understand the present invention, not intended to limit the scope of the present invention in any manner.

Example 1: Preparation of 3-((2S,3R)-2-azido-3-(2,3-dihydrobenzo[b][1,4]dioxin-6-yl)-3-hydroxypropanoyl)-4-phenyloxazolidin-2-one (Compound III-1)

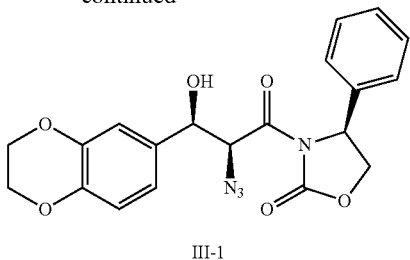

III-1

10 mmol Compound I (wherein $R_1$ and $R_2$ are hydrogen, $R_4$ is phenyl) was dissolved in 100 ml dichloromethane, to which 12 mmol titanium tetrachloride was added dropwise at −78° C. After the mixture was stirred for 20 minutes, 15 mmol DIPEA was added. After the mixture was further stirred for 3 hours, 20 mmol N-methyl pyrrolidone was added. After the addition was completed, the reaction mixture was stirred for 30 minutes, and then 15 mmol 2,3-dihydrobenzo[b][1,4]dioxin-6-formaldehyde was added. After the addition was completed, the reaction mixture was maintained for 30 minutes. The reaction mixture was warmed to −20 to 30° C. and maintained for 2 hours at the temperature. Subsequently, saturated ammonium chloride aqueous solution was added to quench the reaction. The reaction mixture was extracted with dichloromethane twice. The organic phases were combined, washed with water, dried and concentrated to give 2.5 g of the product Compound III-1.

$^1$H NMR (400 MHz, CDCl$_3$) δ 7.40-7.26 (m, 5H), 6.99 (d, 1H), 6.91 (dd, 1H), 6.84 (d, 1H), 5.33 (dd, 1H), 5.18 (d, 1H), 5.15-5.13 (m, 1H), 4.59 (t, 1H), 4.25 (dd, 1H), 4.22 (s, 4H); $^{13}$C NMR (101 MHz, CDCl$_3$) δ 168.06, 153.28, 143.56, 143.49, 138.15, 132.56, 129.31, 129.20, 128.96, 126.05, 125.81, 119.24, 117.29, 115.32, 73.70, 70.65, 65.69, 64.35, 64.29, 57.90; HR-MS (ESI) calcd for C$_{20}$H$_{19}$O$_6$N$_4$(M+H)$^+$: 411.1305, found 411.1312.

Example 2: Preparation of (S)-3-((2S,3R)-2-azido-3-(2,3-dihydrobenzo[b][1,4]dioxin-6-yl)-3-((trimethylsilyl)oxy)propanoyl)-4-phenyloxazolidin-2-one (Compound IV, wherein $R_1$ and $R_2$ are hydrogen, $R_4$ is phenyl, $R_5$ is trimethylsilyl)

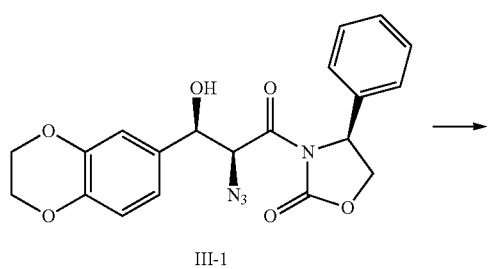

III-1

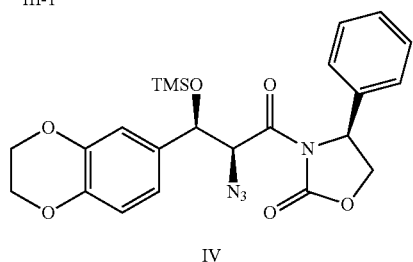

IV 10 mmol Compound III-1 (wherein $R_1$ and $R_2$ are hydrogen, $R_4$ is phenyl, $R_5$ is hydrogen) was dissolved in 200 ml dichloromethane, to which 12 mmol triethylamine was added at 0° C., and then 11 mmol trimethylsilyl chloride was added slowly. After the addition was completed, the reaction was maintained for 3 hours. The reaction mixture was quenched by adding water. Organic phase was dried and concentrated to give 4.3 g of Compound IV (wherein $R_1$ and $R_2$ are hydrogen, $R_4$ is phenyl, $R_5$ is trimethylsilyl).

$^1$H NMR (400 MHz, CDCl$_3$) δ 7.40-7.26 (m, 5H), 6.99 (d, 1H), 6.91 (dd, 1H), 6.83 (d, 1H), 5.24 (dd, 1H), 5.12 (d, 1H), 5.05 (d, 1H), 4.51 (t, 1H), 4.29-4.26 (m, 1H), 4.24 (s, 4H), 0.07 (s, 9H); $^{13}$C NMR (101 MHz, CDCl$_3$) 167.86, 153.04, 143.34, 143.28, 138.11, 133.37, 129.30, 128.96, 125.78, 119.41, 116.98, 115.48, 75.30, 70.46, 66.08, 64.33, 64.30, 57.90, −0.29; HR-MS (ESI) calcd for C$_{23}$H$_{27}$O$_6$N$_4$ (M+H)$^+$: 483.1700, found 483.1717.

Example 3: Preparation of (S)-3-((2S,3R)-2-azido-3-((tert-butyldimethylsilyl)oxy)-3-(2,3-dihydrobenzo[b][1,4]dioxin-6-yl)propanoyl)-4-phenyloxazolidin-2-one (Compound IV, wherein $R_1$ and $R_2$ are hydrogen, $R_4$ is phenyl, $R_5$ is tert-butyldimethylsilyl)

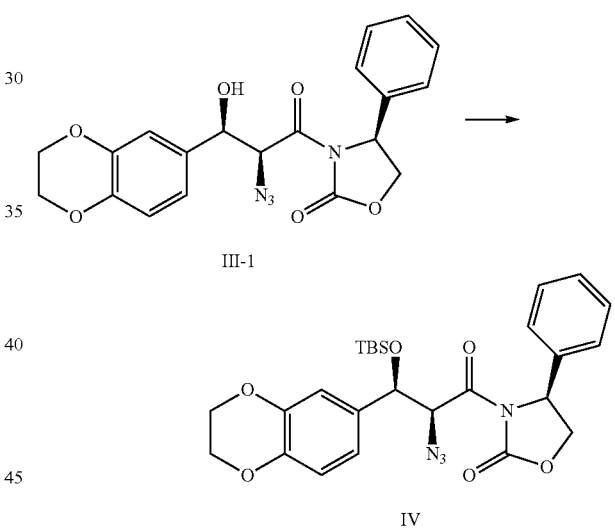

10 mmol Compound III-1 (wherein $R_1$ and $R_2$ are hydrogen, $R_4$ is phenyl, $R_5$ is hydrogen) was dissolved in 200 ml dichloromethane, to which 12 mmol triethylamine was added at 0° C., and then 11 mmol tert-butyldimethylsilyl chloride was added slowly. After the addition was completed, the reaction was maintained for 3 hours. The reaction mixture was quenched by adding water. Organic phase was dried and concentrated to give 4.8 g of Compound IV (wherein $R_1$ and $R_2$ are hydrogen, $R_4$ is phenyl, $R_5$ is tert-butyldimethylsilyl).

$^1$H NMR (400 MHz, CDCl$_3$) δ 7.33-7.22 (m, 3H), 7.20-7.13 (m, 3H), 6.97 (d, 1H), 6.90 (d, 1H), 5.67 (ddt, 1H), 5.44 (dt, 1H), 4.47-4.40 (m, 2H), 4.28-4.17 (m, 4H), 4.10 (dd, 1H), 0.85 (s, 7H), −0.06 (s, 4H); $^{13}$C NMR (101 MHz, CDCl$_3$) δ 171.90, 154.26, 143.28, 143.18, 137.83, 133.03, 128.25, 128.02, 127.45, 120.01, 114.41, 112.33, 76.73, 69.67, 63.72, 63.26, 63.20, 57.36, 25.61, 17.98, −4.77; HR-MS (ESI) calcd for C$_{26}$H$_{32}$O$_6$N$_4$Si (M+H)$^+$: 524.2091, found 524.2084.

Example 4: Preparation of (1R,2R)-2-azido-1-(2,3-dihydrobenzo[b][1,4]dioxin-6-yl)propane-1,3-diol (Compound XI)

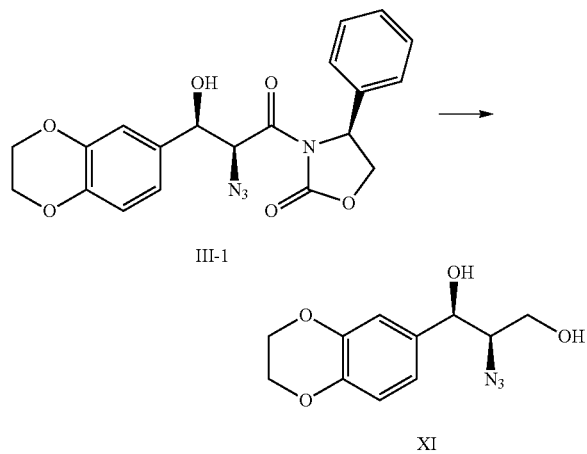

7 mmol Compound III-1 was dissolved in a mixed solvent of 60 ml tetrahydrofuran and 10 ml water, to which 35 mmol sodium borohydride was added at 0° C. After the addition was completed, the reaction mixture was warmed to 25° C. and maintained for 3 hours at the temperature. After the reaction was completed, saturated ammonium chloride solution was added to quench the reaction, and the reaction mixture was extracted with ethyl acetate twice. The combined organic phases were washed with sodium bicarbonate solution, dried and concentrated to give 1.7 g of Compound XI.

$^1$H NMR (400 MHz, CDCl$_3$) δ 6.80-6.89 (m, 3H), 4.66 (d, J=6.8 Hz, 1H), 4.25 (m, 4H), 3.59-3.66 (m, 2H), 3.50-3.57 (m, 1H); $^{13}$C NMR (101 MHz, CDCl$_3$) δ 143.4, 133.5, 118.9, 117.7, 114.8, 74.1, 68.8, 64.0, 62.9; HR-MS (ESI) calcd for C$_{11}$H$_{14}$O$_4$N$_3$ (M+H)$^+$: 252.0984, found 252.0988.

Example 5: Preparation of (2R,3R)-2-azido-3-(2,3-dihydrobenzo[b][1,4]dioxin-6-yl)-3-((trimethylsilyl)oxy)propane-1-ol (Compound V, wherein R$_5$ is trimethylsilyl)

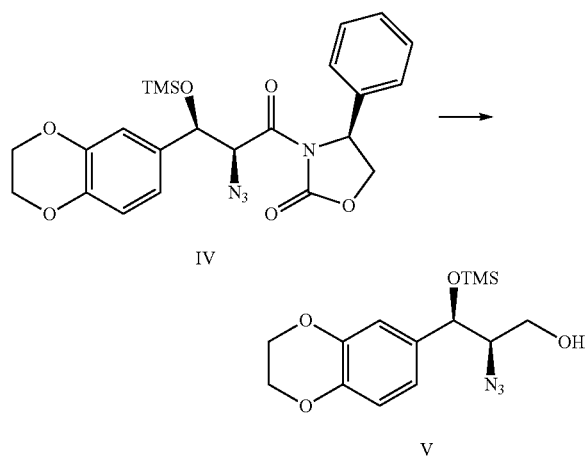

7 mmol Compound IV was dissolved in a mixed solvent of 60 ml tetrahydrofuran and 10 ml water, to which 35 mmol sodium borohydride was added at 0° C. After the addition was completed, the reaction mixture was warmed to 25° C. and maintained for 3 hours at the temperature. After the reaction was completed, saturated ammonium chloride solution was added to quench the reaction, and the reaction mixture was extracted with ethyl acetate twice. The combined organic phases were washed with sodium bicarbonate solution, dried and concentrated to give 2.5 g of Compound V.

$^1$H NMR (400 MHz, CDCl$_3$) δ 7.09-7.00 (m, 2H), 6.88 (d, 1H), 4.73-4.68 (m, 1H), 4.28-4.17 (m, 4H), 3.62-3.53 (m, 1H), 3.42-3.31 (m, 2H), 2.68 (t, 1H), 0.16 (s, 7H).; $^{13}$C NMR (101 MHz, CDCl$_3$) δ 143.14, 143.12, 133.45, 119.83, 114.35, 112.44, 76.61, 68.15, 63.63, 63.60, 62.78, −0.26; HR-MS (ESI) calcd for C$_{14}$H$_{21}$O$_4$N$_3$Si (M+H)$^+$: 323.1301, found 323.1321.

Example 6: Preparation of (2R,3R)-2-azido-3-((tert-butyldimethylsilyl)oxy)-3-(2,3-dihydrobenzo[b][1,4]dioxin-6-yl)propane-1-ol (Compound V, wherein R$_5$ is tert-butyldimethylsilyl)

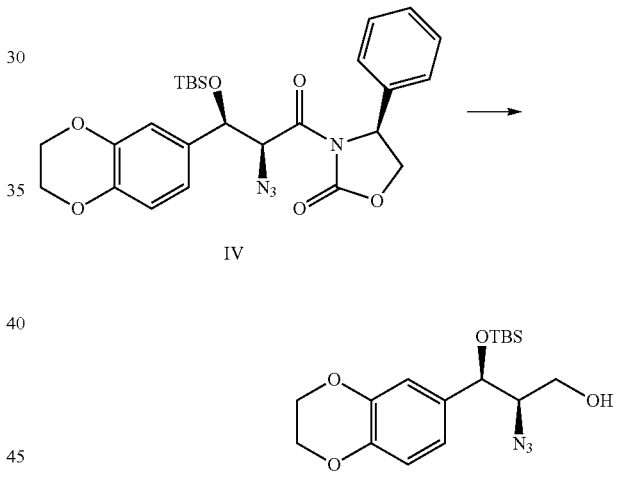

7 mmol Compound IV was dissolved in a mixed solvent of 60 ml tetrahydrofuran and 10 ml water, to which 35 mmol sodium borohydride was added at 0° C. After the addition was completed, the reaction mixture was warmed to 25° C. and maintained for 3 hours at the temperature. After the reaction was completed, saturated ammonium chloride solution was added to quench the reaction, and the reaction mixture was extracted with ethyl acetate twice. The combined organic phases were washed with sodium bicarbonate solution, dried and concentrated to give 2.8 g of Compound V.

$^1$H NMR (400 MHz, CDCl$_3$) δ 7.09-7.02 (m, 2H), 6.88 (d, 1H), 4.85-4.80 (m, 1H), 4.28-4.17 (m, 4H), 3.69 (ddd, 1H), 3.60 (td, 1H), 3.50 (ddd, 1H), 2.68 (t, 1H), 0.84 (s, 6H), 0.02 (s, 4H); $^{13}$C NMR (101 MHz, CDCl$_3$) δ 143.14, 143.14, 133.42, 119.89, 114.34, 112.39, 76.07, 68.60, 63.47, 63.44, 62.45, 25.59, 18.00, −4.76; HR-MS (ESI) calcd for C$_{17}$H$_{27}$O$_4$N$_3$Si (M+H)$^+$: 365.1771, found 365.1782.

Example 7: Preparation of (1R,2S)-2-azido-1-(2,3-dihydrobenzo[b][1,4]dioxin-6-yl)-3-oxo-3-((S)-2-oxo-4-phenyloxazolidin-3-yl)propyl benzoate (Compound IV, wherein $R_1$ and $R_2$ are hydrogen, $R_4$ is phenyl, $R_5$ is benzoyl)

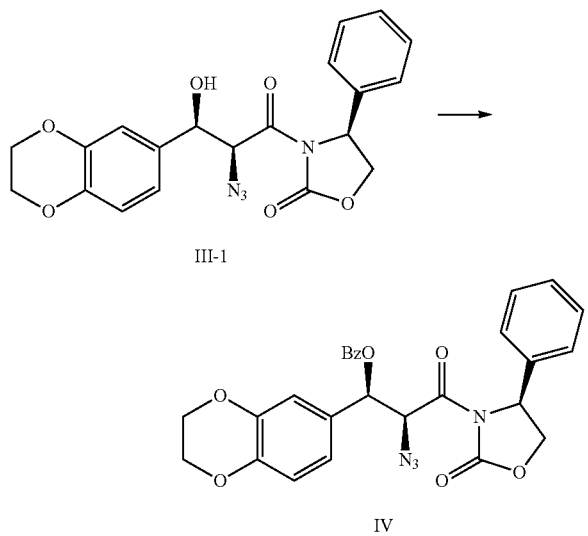

10 mmol Compound III-1 (wherein $R_1$ and $R_2$ are hydrogen, $R_4$ is phenyl, $R_5$ is hydrogen) was dissolved in 200 ml dichloromethane, to which 12 mmol triethylamine was added at 0° C., and then 11 mmol benzoyl chloride was added slowly. After the addition was completed, the reaction was maintained for 3 hours. The reaction mixture was quenched by adding water. Organic phase was dried and concentrated to give 4.9 g of Compound VI (wherein $R_1$ and $R_2$ are hydrogen, $R_4$ is phenyl, $R_5$ is benzoyl).

$^1$H NMR (400 MHz, CDCl$_3$) δ 8.17-8.07 (m, 2H), 7.62-7.56 (m, 1H), 7.49-7.45 (m, 2H), 7.40-7.33 (m, 3H), 7.30-7.27 (m, 2H), 7.13 (s, 1H), 7.06 (dd, 1H), 6.89 (d, 1H), 6.62 (d, 1H), 5.30-5.27 (m, 2H), 4.80 (t, 1H), 4.35 (dd, 1H), 4.25 (s, 4H); $^{13}$C NMR (101 MHz, CDCl$_3$) δ 167.55, 165.53, 153.74, 143.86, 143.58, 138.17, 134.56, 133.66, 130.56, 130.03, 129.28, 129.19, 128.96, 128.94, 128.88, 128.61, 125.91, 119.49, 117.54, 115.48, 74.88, 70.88, 68.31, 64.42, 64.34, 64.30, 58.11; HR-MS (ESI) calcd for C$_{27}$H$_{23}$O$_7$N$_4$ (M+H)$^+$: 515.1567, found 515.1558.

Example 8: Preparation of (1R,2R)-2-azido-1-(2,3-dihydrobenzo[b][1,4]dioxin-6-yl)propane-1,3-diol (Compound XI)

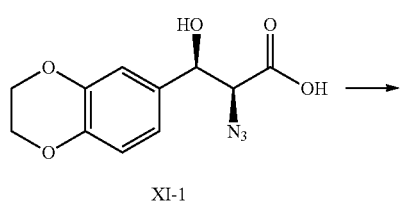

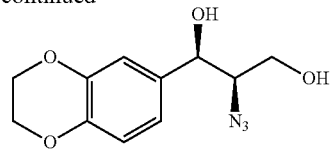

7 mmol Compound XI-1 was dissolved in 60 ml tetrahydrofuran, to which 14 mmol sodium borohydride and 8 mmol boron trifluoride etherate were added at 0° C. After the addition was completed, the reaction mixture was stirred for 3 hours while the temperature was maintained. After the reaction was completed, dilute hydrochloric acid was added to quench the reaction, and the reaction mixture was extracted with ethyl acetate twice. The combined organic phases were washed with sodium bicarbonate solution, dried and concentrated to give 1.4 g of Compound XI.

$^1$H NMR (400 MHz, CDCl$_3$) δ 6.80-6.89 (m, 3H), 4.66 (d, J=6.8 Hz, 1H), 4.25 (m, 4H), 3.59-3.66 (m, 2H), 3.50-3.57 (m, 1H); $^{13}$C NMR (101 MHz, CDCl$_3$) δ 143.4, 133.5, 118.9, 117.7, 114.8, 74.1, 68.8, 64.0, 62.9; HR-MS (ESI) calcd for C$_{11}$H$_{14}$O$_4$N$_3$ (M+H)$^+$: 252.0984, found 252.0988.

Example 9: Preparation of (2R,3R)-2-azido-3-(2,3-dihydrobenzo[b][1,4]dioxin-6-yl)-3-((trimethylsilyl)oxy)propyl 4-methylbenzenesulfonate (Compound VI, wherein $R_5$ is trimethylsilyl)

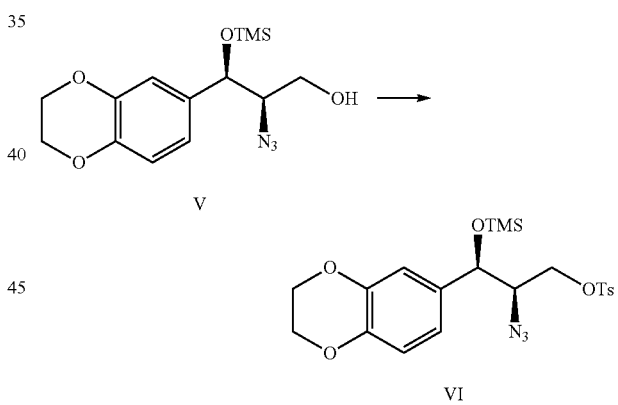

9 mmol Compound V (wherein $R_5$ is trimethylsilyl) was dissolved in 200 ml dichloromethane, to which 12 mmol triethylamine and 10 mg DMAP were added at 0° C. 10 mmol p-toluenesulfonyl chloride was added slowly. After the addition was completed, the reaction was maintained for 3 hours. The reaction mixture was quenched by adding water. Organic phase was dried and concentrated to give 3.7 g of Compound VI (wherein $R_5$ is trimethylsilyl).

$^1$H NMR (400 MHz, CDCl$_3$) δ 7.75-7.73 (m, 2H), 7.34-7.32 (m, 2H), 6.78-6.76 (m, 2H), 6.68 (dd, 1H), 4.58 (d, 1H), 4.24 (s, 4H), 3.93 (dd, 1H), 3.71 (dd, 1H), 3.55-3.51 (m, 1H), 2.44 (s, 3H), 0.00 (s, 9H); $^{13}$C NMR (101 MHz, cdcl$_3$) δ 145.07, 143.56, 143.49, 133.13, 132.44, 129.88, 127.97, 119.43, 117.30, 115.32, 74.63, 68.37, 65.95, 64.29, 64.27, 26.89, −0.12; HR-MS (ESI) calcd for C$_{21}$H$_{28}$O$_6$N$_3$SSi (M+H)$^+$: 478.1468, found 478.1463.

Example 10: Preparation of (2R,3R)-2-azido-3-((tert-butyldimethylsilyl)oxy)-3-(2,3-dihydrobenzo[b][1,4]dioxin-6-yl)propyl 4-methylbenzenesulfonate (Compound VI, wherein $R_5$ is tert-butyldimethylsilyl)

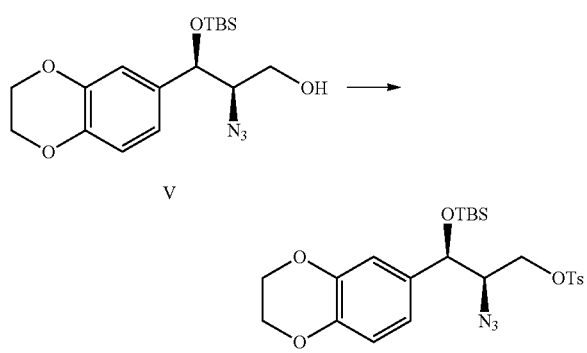

9 mmol Compound V (wherein $R_5$ is tert-butyldimethylsilyl) was dissolved in 200 ml dichloromethane, to which 12 mmol triethylamine and 10 mg DMAP were added at 0° C. 10 mmol p-toluenesulfonyl chloride was added slowly. After the addition was completed, the reaction was maintained for 3 hours. The reaction mixture was quenched by adding water. Organic phase was dried and concentrated to give 4.2 g of Compound VI (wherein $R_5$ is tert-butyldimethylsilyl).

$^1$H NMR (400 MHz, CDCl$_3$) δ 7.75-7.69 (m, 2H), 7.48 (dq, 2H), 7.12 (dd, 1H), 6.95 (d, 1H), 6.90 (d, 1H), 4.74 (d, 1H), 4.28-4.17 (m, 5H), 3.96 (dd, 1H), 3.61 (q, 1H), 2.37 (d, 3H), 0.85 (s, 7H), −0.06 (s, 4H); $^{13}$C NMR (101 MHz, CDCl$_3$) δ 143.59, 143.21, 143.16, 134.03, 133.24, 129.69, 128.09, 120.03, 114.38, 112.44, 76.17, 68.10, 66.52, 63.59, 63.56, 25.61, 21.53, 17.98, −4.80; HR-MS (ESI) calcd for C$_{24}$H$_{33}$O$_6$N$_3$SSi (M+H): 519.1859, found 519.1866.

Example 11: Preparation of (2R,3R)-2-azido-3-(2,3-dihydrobenzo[b][1,4]dioxin-6-yl)-3-hydroxypropyl 4-methylbenzenesulfonate (Compound VI, wherein $R_5$ is hydrogen)

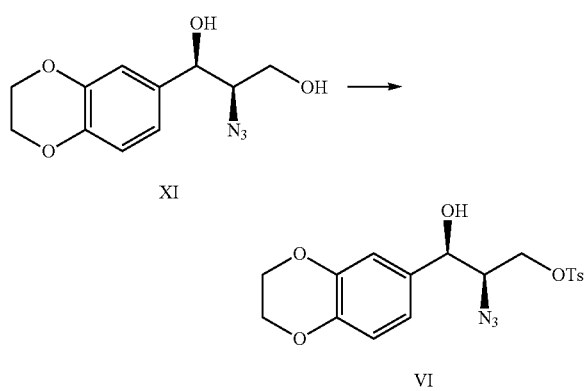

9 mmol Compound XI (wherein $R_5$ is hydrogen) was dissolved in 200 ml dichloromethane, to which 12 mmol triethylamine and 10 mg DMAP were added at 0° C. 10 mmol p-toluenesulfonyl chloride was added slowly. After the addition was completed, the reaction was maintained for 3 hours. The reaction mixture was quenched by adding water. Organic phase was dried and concentrated to give 3.5 g of Compound VI (wherein $R_5$ is hydrogen).

$^1$H NMR (400 MHz, CDCl$_3$) δ 7.81 (d, J=8.4 Hz, 2H), 7.37 (d, J=8.4 Hz, 2H), 6.75-6.87 (m, 3H), 4.60 (d, J=6.4 Hz, 1H), 4.28 (s, 4H), 4.11 (dd, J=3.6 Hz, 10.4 Hz, 1H), 3.90 (dd, J=7.2 Hz, 10.4 Hz, 1H), 3.67-3.71 (m, 1H), 2.45 (s, 3H); $^{13}$C NMR (101 MHz, CDCl$_3$) δ 145.5, 144.2, 143.9, 132.1, 129.7, 128.3, 119.0, 117.9, 114.8, 73.1, 69.1, 65.7, 64.1; HR-MS (ESI) calcd for C$_{18}$H$_{20}$O$_6$N$_3$S (M+H)$^+$: 406.1037, found 406.1035.

Example 12: Preparation of 1-((2R,3R)-2-azido-3-(2,3-dihydrobenzo[b][1,4]dioxin-6-yl)-3-((trimethylsilyl)oxy)propyl)pyrrolidine (Compound VII, wherein $R_5$ is trimethylsilyl)

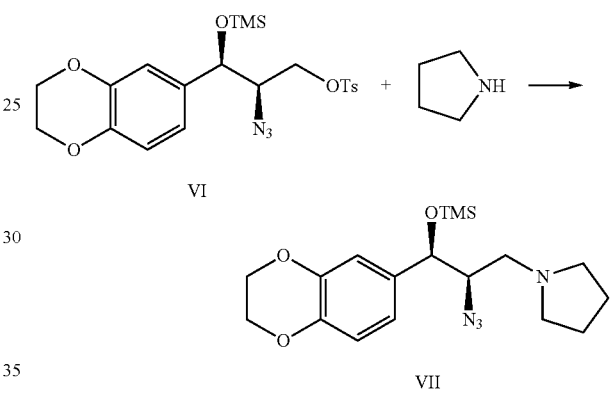

5 mmol Compound VI (wherein $R_5$ is trimethylsilyl) was dissolved in 50 ml DMF, to which 15 mmol pyrrolidine was added. The reaction was stirred at 60° C. for 10 hours. After the reaction was completed, water was added to quench the reaction, and the reaction mixture was extracted with ethyl acetate twice. The combined organic phases were washed with water, dried and concentrated to give 1.0 g of Compound VII (wherein $R_5$ is trimethylsilyl).

$^1$H NMR (400 MHz, CDCl$_3$) δ 6.82-5.74 (m, 3H), 4.60 (d, 1H), 4.23 (s, 4H), 3.44-3.39 (m, 1H), 2.52-2.41 (m, 5H), 2.33 (dd, 1H), 1.75-1.72 (m, 4H), 0.03 (s, 9H); $^{13}$C NMR (101 MHz, CDCl$_3$) δ 160.05, 139.96, 128.98, 128.47, 125.97, 72.29, 64.26, 64.19, 56.28, 54.07, 23.45, 21.74, 0.09; HR-MS (ESI) calcd for C$_{18}$H$_{31}$O$_3$N$_2$Si (M+H)$^+$: 376.1931, found 376.1940.

Example 13: Preparation of (1R,2R)-2-azido-1-(2,3-dihydrobenzo[b][1,4]dioxin-6-yl)-3-(pyrrolidin-1-yl)propane-1-ol (Compound XII)

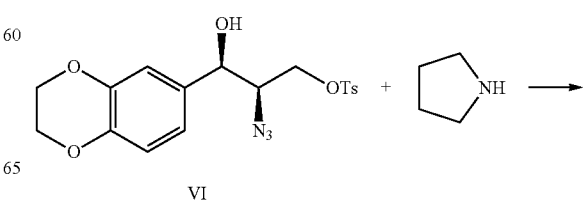

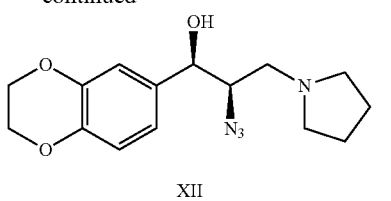

XII 5 mmol Compound VI (wherein $R_5$ is hydrogen) was dissolved in 50 ml DMF, to which 15 mmol pyrrolidine was added. The reaction was stirred at 60° C. for 10 hours. After the reaction was completed, water was added to quench the reaction, and the reaction mixture was extracted with ethyl acetate twice. The combined organic phases were washed with water, dried and concentrated to give 1.1 g of Compound XII.

$^1$H NMR (400 MHz, CDCl$_3$) δ 6.82-6.92 (m, 3H), 4.93 (m, 1H), 4.24 (s, 4H), 4.10 (m, 1H), 3.15-3.19 (m, 1H), 3.07 (m, 4H), 2.81-2.87 (m, 1H), 1.96 (m, 4H); $^{13}$C NMR (101 MHz, CDCl$_3$) δ 143.7, 134.1, 119.8, 117.5, 115.9, 75.5, 64.1, 63.9, 56.7, 54.4, 23.8; HR-MS (ESI) calcd for C$_{15}$H$_{21}$O$_3$ N$_4$(M+H)$^+$: 305.1608, found 305.1611.

Example 14: Preparation of 1-((2R,3R)-2-azido-3-((tert-butyldimethylsilyl)oxy)-3-(2,3-dihydrobenzo[b][1,4]dioxin-6-yl)propyl)pyrrolidine (Compound XII)

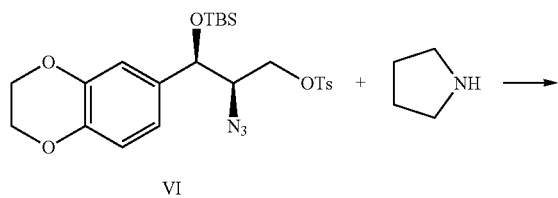

5 mmol Compound VI (wherein $R_5$ is tert-butyldimethylsilyl) was dissolved in 50 ml DMF, to which 15 mmol pyrrolidine was added. The reaction was stirred at 60° C. for 10 hours. After the reaction was completed, water was added to quench the reaction, and the reaction mixture was extracted with ethyl acetate twice. The combined organic phases were washed with water, dried and concentrated to give 2.1 g of Compound XII.

$^1$H NMR (400 MHz, CDCl$_3$) δ 7.09-7.02 (m, 2H), 6.88 (d, 1H), 4.75-4.70 (m, 1H), 4.28-4.17 (m, 4H), 3.47 (q, 1H), 2.93-2.79 (m, 4H), 2.53 (dd, 1H), 2.02 (dd, 1H), 1.84 (hept, 4H), 0.84 (s, 7H), 0.02 (s, 4H); $^{13}$C NMR (101 MHz, CDCl$_3$) δ 143.18, 143.15, 132.60, 120.03, 114.34, 112.38, 78.23, 63.80, 63.78, 63.69, 59.99, 54.51, 25.61, 23.73, 18.03, −4.78; HR-MS (ESI) calcd for C$_{21}$H$_{34}$O$_3$N$_4$Si (M+H)$^+$: 418.2400, found 418.2413.

Example 15: Preparation of (1R,2R)-1-(2,3-dihydrobenzo[b][1,4]dioxin-6-yl)-3-(pyrrolidin-1-yl)-1-((trimethylsilyl)oxy)propan-2-amine (Compound VIII, wherein $R_5$ is trimethylsilyl)

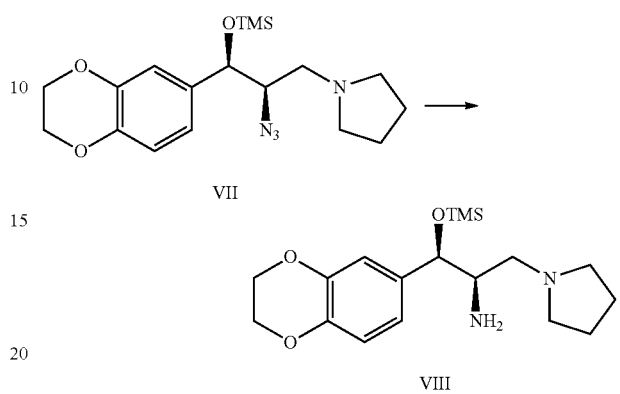

4 mmol Compound VII (wherein $R_5$ is trimethylsilyl) was dissolved in 200 ml methanol, to which 20 mg of 5% Pd/C was added. The reaction was carried out under 0.1 MPa of hydrogen pressure at 25° C. for 10 hours. After the reaction was completed, the reaction mixture was filtrated and concentrated to give 1.3 g of Compound VIII (wherein $R_5$ is trimethylsilyl).

$^1$H NMR (400 MHz, CDCl$_3$) δ 7.15-7.10 (m, 1H), 7.07-7.00 (m, 1H), 6.88 (d, 1H), 4.46 (d, 1H), 4.28-4.17 (m, 4H), 3.59 (d, 2H), 3.25 (qt, 1H), 2.91-2.77 (m, 4H), 2.49 (dd, 1H), 2.40 (dd, 1H), 1.89-1.80 (m, 4H), 0.16 (s, 7H); $^{13}$C NMR (101 MHz, CDCl$_3$) δ 143.16, 142.99, 134.17, 120.00, 114.33, 112.41, 78.06, 63.52, 63.50, 61.58, 54.57, 53.62, 23.64, −0.26; HR-MS (ESI) calcd for C$_{18}$H$_{30}$O$_3$ N$_2$Si (M+H)$^+$: 350.2026, found 350.2032.

Example 16: Preparation of (1R,2R)-2-amino-1-(2,3-dihydrobenzo[b][1,4]dioxin-6-yl)-3-(pyrrolidin-1-yl)propane-1-ol (Compound VIII, wherein $R_5$ is hydrogen)

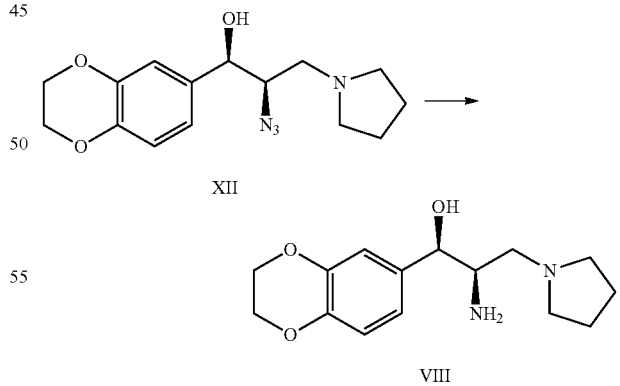

2 mmol Compound XII (wherein $R_5$ is hydrogen) was dissolved in 100 ml methanol, to which 10 mg of 5% Pd/C was added. The reaction was carried out under 0.1 MPa of hydrogen pressure at 25° C. for 10 hours. After the reaction was completed, the reaction mixture was filtrated and concentrated to give 0.6 g of Compound VIII (wherein $R_5$ is hydrogen).

¹H NMR (400 MHz, CDCl₃) δ 6.77-6.85 (m, 3H), 5.85 (d, J=7.2 Hz, 1H), 4.91 (d, J=3.6 Hz, 1H), 4.23 (s, 4H), 4.15-4.21 (m, 1H), 2.74-2.83 (m, 2H), 2.61-2.67 (m, 4H), 2.07-2.11 (m, 2H), 1.79-1.81 (m, 4H), 1.51-1.56 (m, 2H), 1.22-1.33 (m, 10H), 0.89 (t, J=6.8 Hz, 3H); ¹³C NMR (101 MHz, CDCl₃) δ 174.1, 143.2, 142.7, 134.6, 119.2, 117.3, 115.1, 75.6, 64.5, 57.9, 55.1, 52.0, 36.5, 31.7, 29.5, 29.1, 25.8, 23.4, 22.7, 13.9. HR-MS (ESI) calcd for $C_{23}H_{37}O_4N_2(M+H)^+$: 405.2748, found 405.2741.

Example 17: Preparation of (1R,2R)-1-((tert-butyldimethylsilyl)oxy)-1-(2,3-dihydrobenzo[b][1,4]dioxin-6-yl)-3-(pyrrolidin-1-yl)propan-2-amine (Compound VIII, wherein $R_5$ is tert-butyldimethylsilyl)

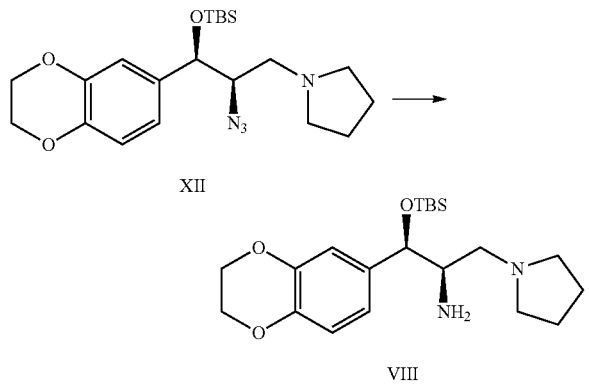

2 mmol Compound XII (wherein $R_5$ is tert-butyldimethylsilyl) was dissolved in 100 ml methanol, to which 10 mg of 5% Pd/C was added. The reaction was carried out under 0.1 MPa of hydrogen pressure at 25° C. for 10 hours. After the reaction was completed, the reaction mixture was filtrated and concentrated to give 1.1 g of Compound VIII (wherein $R_5$ is tert-butyldimethylsilyl).

¹H NMR (400 MHz, CDCl₃) δ 7.14-7.09 (m, 1H), 7.03 (dd, 1H), 6.88 (d, 1H), 4.67 (dt, 1H), 4.28-4.17 (m, 4H), 3.59 (d, 2H), 3.24 (qt, 1H), 2.92-2.77 (m, 4H), 2.74 (dd, 1H), 2.40 (dd, 1H), 1.89-1.80 (m, 4H), 0.84 (s, 7H), 0.01 (s, 4H); ¹³C NMR (101 MHz, CDCl₃) δ 143.17, 143.04, 134.13, 120.03, 114.33, 112.46, 76.86, 63.55, 63.52, 61.53, 54.58, 53.69, 25.61, 23.74, 17.89, −4.79; HR-MS (ESI) calcd for $C_{21}H_{36}O_3N_2Si (M+H)^+$: 392.2495, found 392.2483.

Example 18: Preparation of N-((1R,2R)-1-(2,3-dihydrobenzo[b][1,4]dioxin-6-yl)-1-((trimethylsilyl)oxy)-3-(pyrrolidin-1-yl)propan-2-yl)octanamide (Compound X, wherein $R_5$ is trimethylsilyl)

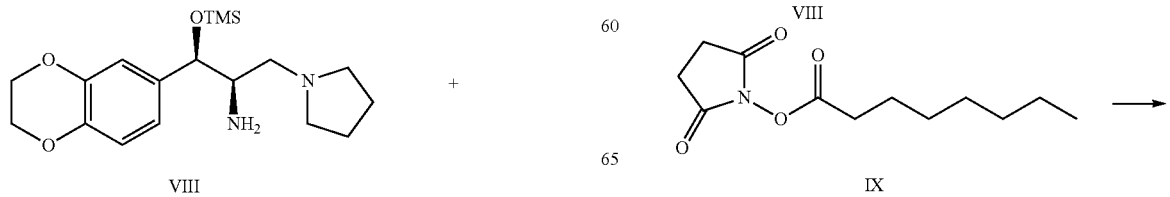

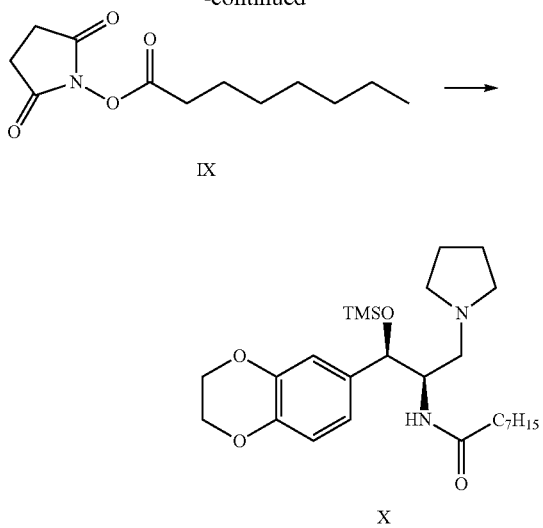

1 mmol Compound VIII (wherein $R_5$ is trimethylsilyl) was dissolved in 30 ml DMF, to which 1.5 mmol DIPEA and 1.2 mmol Compound IX (wherein $R_6$ is succimidyloxy) were added. After the addition was completed, the reaction was maintained at 25° C. for 24 hours. After the reaction was completed, water was added to quench the reaction, and the reaction mixture was extracted with ethyl acetate twice. The combined organic phases were washed with water, dried and concentrated to give 0.5 g of Compound X.

¹H NMR (400 MHz, CDCl₃) δ 6.76-6.59 (m, 3H), 5.77 (d, 1H), 5.01 (d, 1H), 4.16 (s, 3H), 4.06 (q, 1H), 3.99 (dtd, 1H), 2.63 (dd, 1H), 2.58-2.38 (m, 4H), 2.24 (dd, 1H), 2.03 (td, 2H), 1.98 (s, 1H), 1.76-1.64 (m, 4H), 1.45 (p, 2H), 1.27-1.09 (m, 8H), 0.82 (t, 3H); ¹³C NMR (101 MHz, CDCl₃) δ 172.55, 171.02, 142.91, 142.34, 135.90, 118.63, 116.57, 114.67, 71.33, 64.26, 64.18, 60.31, 56.47, 55.06, 54.26, 53.94, 36.76, 31.61, 29.03, 29.01, 25.64, 23.59, 22.59, 20.97, 14.14, 14.05, 1.36; HR-MS (ESI) calcd for $C_{18}H_{31}O_3N_2Si (M+H)^+$: 477.3149, found 477.3155.

Example 19: Preparation of N-((1R,2R)-1-((tert-butyldimethylsilyl)oxy)-1-(2,3-dihydrobenzo[b][1,4]dioxin-6-yl)-3-(pyrrolidin-1-yl)propan-2-yl)octanamide (Compound X, wherein $R_5$ is tert-butyldimethyl silyl)

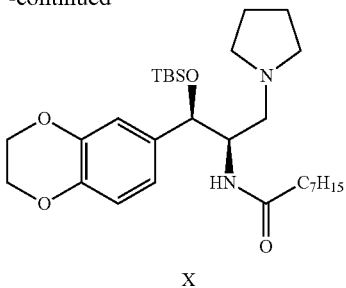

X 1 mmol Compound VIII (wherein $R_5$ is tert-butyldimethylsilyl) was dissolved in 30 ml DMF, to which 1.5 mmol DIPEA and 1.2 mmol Compound IX (wherein $R_6$ is succimidyloxy) were added. After the addition was completed, the reaction was maintained at 25° C. for 24 hours. After the reaction was completed, water was added to quench the reaction, and the reaction mixture was extracted with ethyl acetate twice. The combined organic phases were washed with water, dried and concentrated to give 0.9 g of Compound X.

$^1$H NMR (400 MHz, CDCl$_3$) δ 7.04 (ddd, 1H), 6.91-6.81 (m, 2H), 6.18 (d, 1H), 5.19 (d, 1H), 4.28-4.17 (m, 4H), 4.11 (dq, 1H), 2.91-2.83 (m, 2H), 2.86-2.76 (m, 2H), 2.59 (dd, 1H), 2.51 (dd, 1H), 2.26 (dt, 1H), 2.19 (dt, 1H), 1.83 (p, 4H), 1.63 (dt, 1H), 1.47 (dt, 1H), 1.39-1.14 (m, 7H), 0.94-0.84 (m, 3H), 0.85 (s, 6H), −0.06 (s, 4H); $^{13}$C NMR (101 MHz, CDCl$_3$) δ 174.41, 143.16, 143.13, 134.01, 120.36, 114.37, 112.72, 76.42, 63.59, 63.56, 60.11, 54.61, 54.20, 35.54, 31.26, 28.68, 28.40, 25.62, 25.07, 23.79, 22.79, 17.98, 14.06, −4.76; HR-MS (ESI) calcd for $C_{29}H_{50}O_4N_2Si$ $(M+H)^+$: 518.3540, found 518.3549.

Example 20: Preparation of Eliglustat

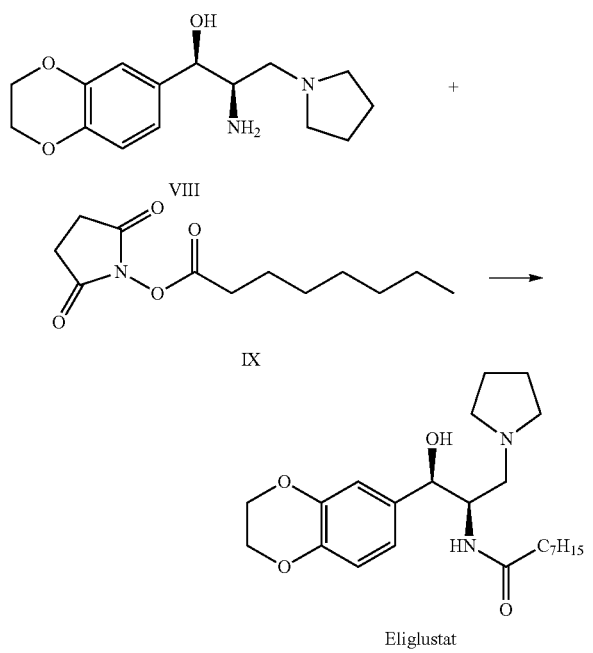

Eliglustat 1 mmol Compound VIII (wherein $R_5$ is hydrogen) was dissolved in 30 ml DMF, to which 1.5 mmol DIPEA and 1.2 mmol Compound IX (wherein $R_6$ is succimidyloxy) were added. After the addition was completed, the reaction was maintained at 25° C. for 24 hours. After the reaction was completed, water was added to quench the reaction, and the reaction mixture was extracted with ethyl acetate twice. The combined organic phases were washed with water, dried and concentrated to give 0.3 g Eliglustat.

$^1$H NMR (400 MHz, CDCl$_3$) δ 6.72-6.90 (m, 3H), 5.83 (d, 1H), 4.89 (d, 1H), 4.25 (m, 4H), 4.15-4.19 (m, 1H), 2.71-2.77 (m, 2H), 2.56-2.70 (m, 4H), 2.10 (t, 2H), 1.73-1.82 (m, 4H), 1.46-1.57 (m, 2H), 1.15-1.30 (m, 8H), 0.88 (t, 3H); $^{13}$C NMR (101 MHz, CDCl$_3$) δ 174.47, 143.25, 143.17, 135.21, 120.41, 114.34, 112.85, 74.96, 63.81, 63.60, 59.47, 54.48, 53.67, 35.86, 31.39, 28.44, 28.27, 25.39, 23.75, 22.71, 14.08. HR-MS (ESI) calcd for $C_{23}H_{37}O_2$ $N_4$ $(M+H)^+$: 405.2753, found 405.2760.

Example 21: Preparation of Eliglustat

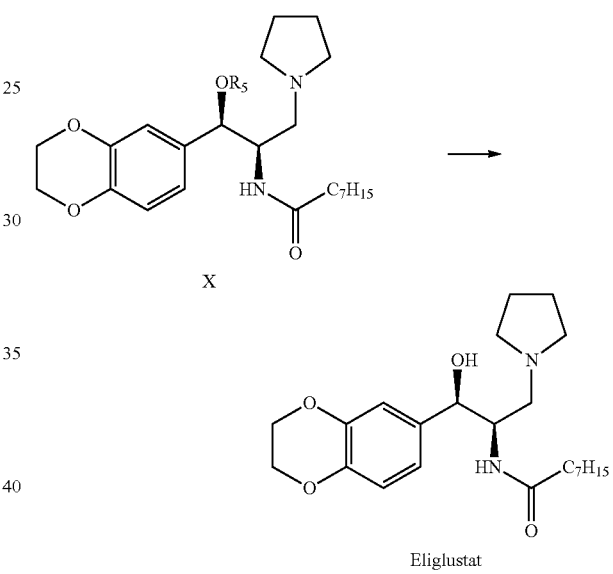

Eliglustat 1 mmol Compound X (wherein $R_5$ is trimethylsilyl) was dissolved in 30 ml THF, to which 20 ml of 2N HCl was added. After the addition was completed, the reaction was maintained at 25° C. for 2 hours. After the reaction was completed, water was added to quench the reaction, and the reaction mixture was extracted with ethyl acetate twice. Organic phases were combined, and washed with saturated sodium bicarbonate solution once. The resulting organic phase was dried and concentrated to give 0.4 g Eliglustat.

$^1$H NMR (400 MHz, CDCl$_3$) δ 6.72-6.90 (m, 3H), 5.83 (d, 1H), 4.89 (d, 1H), 4.25 (m, 4H), 4.15-4.19 (m, 1H), 2.71-2.77 (m, 2H), 2.56-2.70 (m, 4H), 2.10 (t, 2H), 1.73-1.82 (m, 4H), 1.46-1.57 (m, 2H), 1.15-1.30 (m, 8H), 0.88 (t, 3H); $^{13}$C NMR (101 MHz, CDCl$_3$) δ 174.47, 143.25, 143.17, 135.21, 120.41, 114.34, 112.85, 74.96, 63.81, 63.60, 59.47, 54.48, 53.67, 35.86, 31.39, 28.44, 28.27, 25.39, 23.75, 22.71, 14.08. HR-MS (ESI) calcd for $C_{23}H_{37}O_2$ $N_4(M+H)^+$: 405.2753, found 405.2760.

The invention claimed is:
1. A process for preparation of Eliglustat or a pharmaceutically acceptable salt thereof,

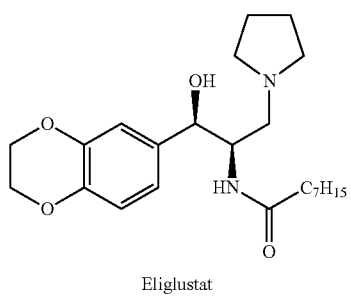

Eliglustat the process comprising the following steps:
(a-3) reducing Compound VII by catalytic hydrogenation with a metal catalyst or reducing Compound VII with organophosphorus reagent, to give Compound VIII,

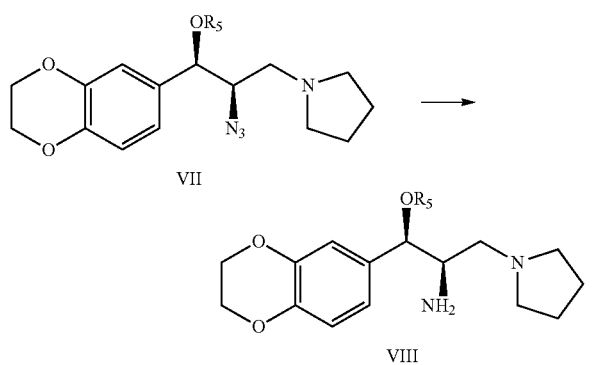

wherein $R_5$ is hydrogen or a hydroxy-protecting group selected from the group consisting of alkyl, haloalkyl, aralkyl, alkoxyalkyl, allyl, acyl and silyl protective group,
(a-4) amidation reaction of Compound VIII with Compound IX to give Compound X,

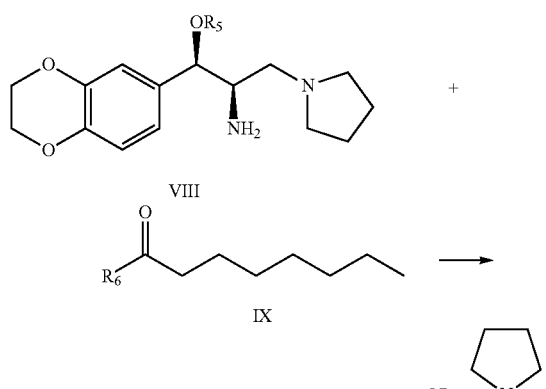

wherein $R_6$ is selected from the group consisting of hydroxy, halogen and succimidyloxy, and wherein $R_5$ is either hydrogen, whereby Compound X is Eliglustat, or $R_5$ is the hydroxy-protecting group and the process further comprises the following step:
(a-5) deprotecting Compound X to remove the hydroxy-protecting group to give Eliglustat

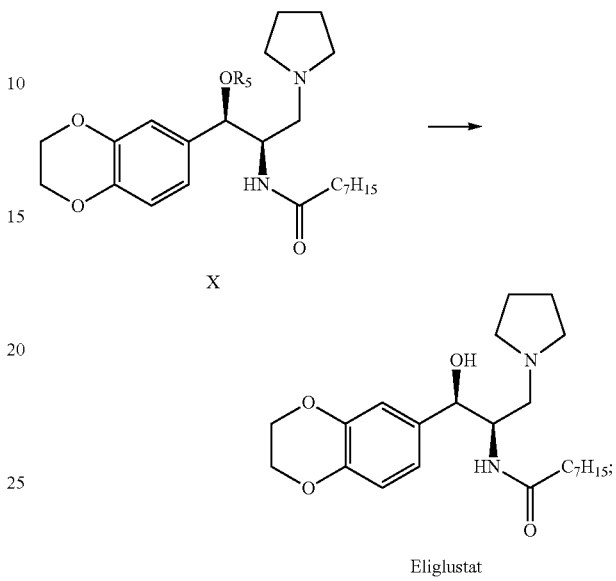

Eliglustat wherein the process comprises the following steps before step (a-3):
(a-1) sulfonylation reaction of Compound V to give Compound VI,

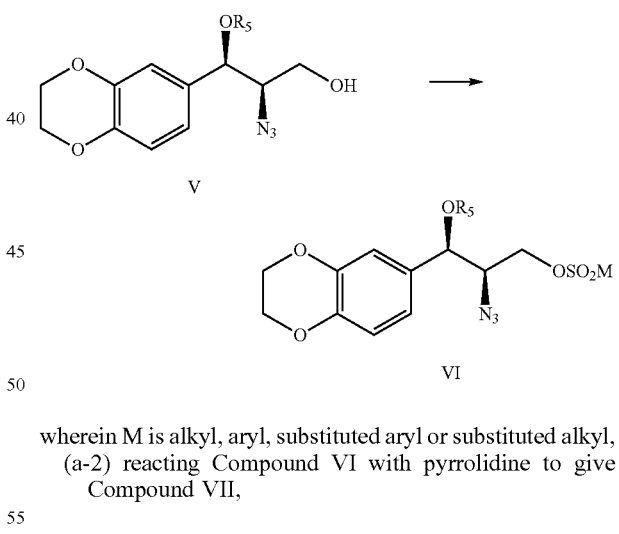

wherein M is alkyl, aryl, substituted aryl or substituted alkyl,
(a-2) reacting Compound VI with pyrrolidine to give Compound VII,

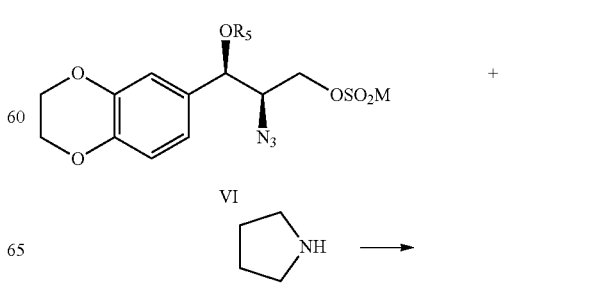

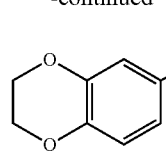

VII and
wherein the process comprises the following steps before step (a-1):
(c-1) coupling reaction of Compound I with Compound II in the presence of Lewis acid, deacid reagent and coordination agent, to give Compound III,

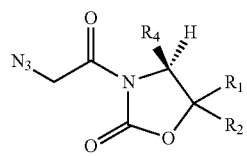

I

II

III wherein each of $R_1$, $R_2$ and $R_4$, independent of each other, is selected from the group consisting of hydrogen, alkyl, aryl and aralkyl,
(c-2) optionally, reacting Compound III with a hydroxy-protecting reagent in the presence of base to give Compound IV,

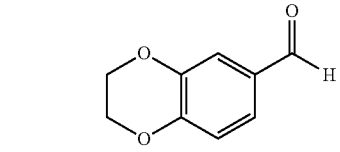

III

IV and
(c-3) preparing the compound of formula V by one of the following steps:
(c-3.1a) reducing Compound III to obtain Compound V wherein $R_5$ is hydrogen

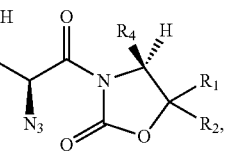

III

V or
(c-3.1b) reducing Compound IV to obtain Compound V wherein $R_5$ is the hydroxy-protecting group

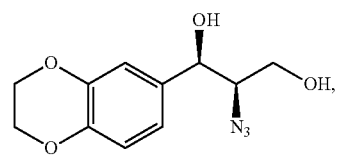

IV

V or
(c-3.2a) oxidizing Compound III to give Compound XI-1, and reducing Compound XI-1 to obtain Compound XI wherein $R_5$ is hydrogen

III

XI-1

XI or (c-3.2b) oxidizing Compound IV to give Compound V-1, and reducing Compound V-1 to obtain Compound V wherein $R_5$ is the hydroxy-protecting group

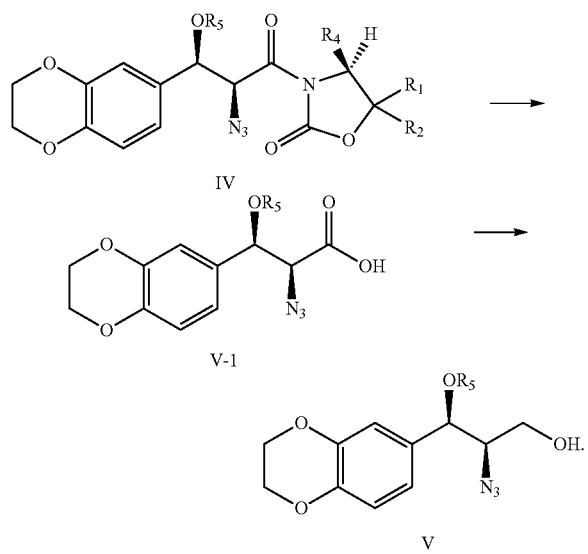

2. The process according to claim 1, wherein in step c-1, the Lewis acid is titanium tetrachloride or tin dichloride, the deacid reagent is an organic base, and the coordination agent is N-methyl pyrrolidone; wherein in optional step c-2, the reaction solvent is an organic aprotic solvent or solvents; wherein in each of steps c-3.1(a) and (b), the reducing is carried out with an reducing agent selected from the group consisting of sodium borohydride, potassium borohydride, boron trifluoride etherate, boranes, and a mixture of any two or more thereof; and wherein in each of steps c-3.2(a) and (b), the oxidizing is carried out with an oxidizing agent that is a peroxide or a manganese-containing salt with or without catalysis of a base selected from the group consisting of alkali metal, alkaline earth metal hydroxide and alkaline earth metal carbonate, and the reducing is carried out with a reducing agent selected from the group consisting of sodium borohydride, potassium borohydride, boron trifluoride etherate, boranes, and a mixture of any two or more thereof.

3. The process according to claim 1, wherein $R_6$ is chloro or succimidyloxy.

4. The process according to claim 1, wherein in step (a-1), the sulfonylation reaction is carried out with sulfonyl halide without a catalyst or with a suitable amount of acylation catalyst.

5. The process according to claim 1, wherein in step (a-2), the pyrrolidine is reacted with the sulfonate of formula VI in an organic aprotic solvent or solvents.

6. The process according to claim 1, wherein in step (a-3), Compound VII is reduced by catalytic hydrogenation with the metal catalyst, wherein the metal catalyst is a Pd catalyst or a Ni catalyst.

7. The process according to claim 1, wherein $R_6$ is hydroxy and the amidation reaction of Compound VIII with Compound IX is carried out under catalysis of a coupling agent for amidation to give Compound X.

8. The process according to claim 1, wherein $R_6$ is chloro or succimidyloxy, and the amidation reaction of Compound VIII with Compound IX yields Compound X.

9. The process according to claim 1, wherein $R_5$ is the silyl protective group, and the reaction of step a-5 is carried out in the presence of an acid, a fluorine-containing salt or a base selected from the group consisting of alkali metal, alkaline earth metal hydroxide and alkaline earth metal carbonate.

10. The process according to claim 1, wherein $R_5$ is an alkyl, haloalkyl, alkoxyalkyl or an allyl protective group and the reaction of step a-5 is carried out in the presence of an acid.

11. The process according to claim 1, wherein $R_5$ is the aralkyl protective group and the reaction of step a-5 is carried out under catalytic hydrogenation with metal catalyst, wherein the metal catalyst is a Pd catalyst or a Ni catalyst.

12. The process according to claim 1, wherein $R_5$ is p-methoxybenzyl and the reaction of step a-5 is carried out in the presence of an oxidizing agent.

13. The process according to claim 1, wherein $R_5$ is an acyl protective group and the reaction of step a-5 removes the acyl from the acyl protective group.

14. The process according to claim 1, wherein $R_5$ is hydrogen, and the process consists of reaction steps (a-1), (a-2), (a-3) and (a-4).

15. A compound of formula V:

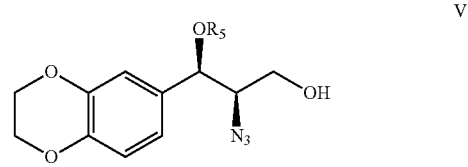

wherein $R_5$ is hydrogen or a hydroxy-protecting group selected from the group consisting of alkyl, haloalkyl, aralkyl, alkoxyalkyl, allyl, acyl and silyl protective group.

16. The compound according to claim 14, having the structure of formula XI:

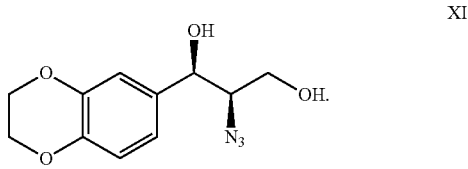 [SMILES: [N-]=[N+]=N[C@H](CO)[C@H](O)c1ccc2c(c1)OCCO2]

17. A compound of formula VII:

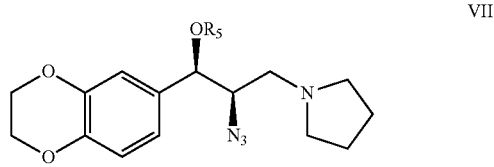

wherein $R_5$ is hydrogen or a hydroxy-protecting group selected from the group consisting of alkyl, haloalkyl, aralkyl, alkoxyalkyl, allyl, acyl and silyl protective group.

18. The compound according to claim 16, having the structure of formula XII
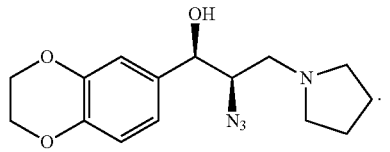
XII
* * * * *